US011560556B2

(12) United States Patent
Fager et al.

(10) Patent No.: US 11,560,556 B2
(45) Date of Patent: Jan. 24, 2023

(54) PROTEIN C-FACTOR VII CHIMERAS

(71) Applicants: DUKE UNIVERSITY, Durham, NC (US); The U.S. Government as Represented by the Department of Veterans Affairs, Washington, DC (US)

(72) Inventors: Ammon Fager, Durham, NC (US); Maureane Hoffman, Durham, NC (US)

(73) Assignees: Duke University, Durham, NC (US); The U.S. Government as Represented by the Department of Veteran Affairs, Washington, DC (US)

( * ) Notice: Subject to any disclaimer, the term of this patent is extended or adjusted under 35 U.S.C. 154(b) by 0 days.

(21) Appl. No.: 17/265,277

(22) PCT Filed: Aug. 3, 2019

(86) PCT No.: PCT/US2019/045018
§ 371 (c)(1),
(2) Date: Feb. 2, 2021

(87) PCT Pub. No.: WO2020/028886
PCT Pub. Date: Feb. 6, 2020

(65) Prior Publication Data
US 2021/0301277 A1 Sep. 30, 2021

Related U.S. Application Data

(60) Provisional application No. 62/714,189, filed on Aug. 3, 2018.

(51) Int. Cl.
*C12N 9/64* (2006.01)
*A61K 38/00* (2006.01)

(52) U.S. Cl.
CPC ......... *C12N 9/6437* (2013.01); *C12N 9/6464* (2013.01); *A61K 38/00* (2013.01); *C07K 2319/00* (2013.01); *C07K 2319/01* (2013.01)

(58) Field of Classification Search
None
See application file for complete search history.

(56) References Cited

U.S. PATENT DOCUMENTS

| 2003/0022354 A1 | 1/2003 | Gerlitz et al. |
| 2008/0260755 A1 | 10/2008 | Metzner et al. |
| 2010/0166729 A9 | 1/2010 | Madison et al. |
| 2012/0064075 A1 | 3/2012 | Strafford et al. |

FOREIGN PATENT DOCUMENTS

| WO | 2008127702 | 10/2008 |
| WO | 2012149463 | 11/2012 |

OTHER PUBLICATIONS

Shi et al. (Thromb. Haemost., 2000, vol. 83, pp. 455-461).*
Aljamali MN, et al. (2008) Long-term expression of murine activated factor VII is safe, but elevated levels cause premature mortality. J. Clin. Invest. 118:1825-1834.
Chang JY, et al. (1995) The roles of factor VII's structural domains in tissue factor binding. Biochemistry 34:12227-12232.
Fager AM, et al. (2018) Human platelets express endothelial protein C receptor, which can be utilized to enhance localization of factor VIIa activity. J. Thromb. Haemost. 16:1817-1829.
Fukudome K, et al. (1994) Identification, cloning, and regulation of a novel endothelial cell protein C/activated protein C receptor. J. Biol. Chem. 269:26486-26491.
Ghosh S, et al. (2007) Endothelial cell protein C receptor acts as a cellular receptor for factor VIIa on endothelium. J. Biol. Chem. 282:11849-11857.
Grandoni J, et al. (2017) Kinetic analysis and binding studies of a new recombinant human factor VIIa for treatment of haemophilia. Haemophilia 23:300-308.
Hedner U. (2000) NovoSeven® as a universal haemostatic agent. Blood Coagulation & Fibrinolysis. 11 (suppl1): S107-S111.
Hoffman M, et al. (2011) Platelet binding and activity of a factor VIIa variant with enhanced tissue factor independent activity. J. Thromb. Haemost. 9:759-766.
Jin J, et al. (1999) Factor VIIa's first epidermal growth factor-like domain's role in catalytic activity. Biochemistry 38:1185-1192.
Kaufman RJ. (1998) Post-translational Modifications Required for Coagulation Factor Secretion and Function. Thromb. Haemost. 79:1068-1079.
Keshava S, et al. (2017) Factor VIIa interaction with EPCR modulates the hemostatic effect of rFVIIa in hemophilia therapy: mode of its action. Blood Adv. 1:1206-1214.
Kisiel W. (1979) Human Plasma Protein C. J. Clin. Invest. 64:761-769.
Kriegler T, et al. (2018) Measuring Endoplasmic Reticulum Signal Sequences Translocation Efficiency Using the Xbp1 Arrest Peptide. Cell Chem. Biol. 25:880-890.
Lazarus RA, et al. (2004) Inhibitors of Tissue Factor-Factor VIIa for Anticoagulant Therapy. Curr. Med. Chem. 11:2275-2290.
Monroe DM, et al. (1997) Platelet activity of high-dose Factor VIIa is independent of tissue factor. Br. J. Haematol. 99:542-547.
Pan LC, et al. (1985) The propeptide of rat bone gamma-carboxyglutamic acid protein shares homology with other vitamin K-dependent protein precursors. Proc. Natl. Acad. Sci. USA 82:6109-6113.
Stanley TB, et al. (1999) The Propeptides of the Vitamin K-dependent Proteins Possess Different Affinities for the Vitamin K-dependent Carboxylase. J. Biol. Chem. 274:16940-1694.
Vavalle JP, et al. (2014) The effect of the REG2 Anticoagulation System on thrombin generation kinetics: a pharmacodynamic and pharmacokinetic first-in-human study. J. Thromb. Thrombolysis 38:275-284.
Von Bruhl ML, et al. (2012) Monocytes, neutrophils, and platelets cooperate to initiate and propagate venous thrombosis in mice in vivo. J. Exp. Med. 209:819-835.
Yank V, et al. (2011) Systematic review: benefits and harms of in-hospital use of recombinant factor VIIa for off-label indications. Ann. Intern Med. 154:529-540.
International Search Report and Written Opinion dated Dec. 11, 2019 for PCT Application No. PCT/US2019/045018 (Applicant—Duke University, et al.) (17 pages).
Ndonwi M, et al. (2007). Substitution of the Gla domain in factor X with that of protein C impairs its interaction with factor VIIa/tissue factor: lack of comparable effect by similar substitution in factor IX. J Biol Chem. 282(21):15632-15644.

(Continued)

*Primary Examiner* — Hope A Robinson
(74) *Attorney, Agent, or Firm* — Polsinelli PC

(57) ABSTRACT

Provided are chimeric Protein C-Factor VII proteins comprising a Gla domain from Protein C (PC), an EGF-1 domain from PC, an EGF-2 domain from Factor VII (FVII), and a protease domain from FVII.

12 Claims, 11 Drawing Sheets

Specification includes a Sequence Listing.

(56) References Cited

OTHER PUBLICATIONS

Gleeson EM, et al. (2017). A novel protein C-factor VII chimera provides new insights into the structural requirements for cytoprotective protease-activated receptor 1 signaling. J Thromb Haemost. 15(11):2198-2207.

Extended European Search Report dated Apr. 22, 2022 for EP Application No. 19845511.5 (nationalized on Feb. 18, 2021) (Applicant—Duke University // Inventor—Ammon Fager, et al.) (8 pages).

* cited by examiner

Factor VII Zymogen

```
1    MVSQALRLLC LLLGLQGCLA AGGVAKASGG ETRDMPWKPG PHRVFVTQEE AHGVLHRRRR
61   ANAFLEELRP GSLERECKEE QCSFEEAREI FKDAERTKLF WISYSDGDQC ASSPCQNGGS
121  CKDQLQSYIC FCLPAFEGRN CETHKDDQLI CVNENGGCEQ YCSDHTGTKR SCRCHEGYSL
181  LADGVSCTPT VEYPCGKIPI LEKRNASKPQ GRIVGGKVCP KGECPWQVLL LVNGAQLCGG
241  TLINTIWVVS AAHCFDKIKN WRNLIAVLGE HDLSEHDGDE QSRRVAQVII PSTYVPGTTN
301  HDIALLRLHQ PVVLTDHVVP LCLPERTFSE RTLAFVRFSL VSGWGQLLDR GATALELMVL
361  NVPRLMTQDC LQQSRKVGDS PNITEYMFCA GYSDGSKDSC KGDSGGPHAT HYRGTWYLTG
421  IVSWGQGCAT VGHFGVYTRV SQYIEWLQKL MRSEPRPGVL LRAPFP (SEQ ID NO: 1)
```

Figure 10A

Factor VII

```
1    ANAFLEELRP GSLERECKEE QCSFEEAREI FKDAERTKLF WISYSDGDQC ASSPCQNGGS
61   CKDQLQSYIC FCLPAFEGRN CETHKDDQLI CVNENGGCEQ YCSDHTGTKR SCRCHEGYSL
121  LADGVSCTPT VEYPCGKIPI LEKRNASKPQ GRIVGGKVCP KGECPWQVLL LVNGAQLCGG
181  TLINTIWVVS AAHCFDKIKN WRNLIAVLGE HDLSEHDGDE QSRRVAQVII PSTYVPGTTN
241  HDIALLRLHQ PVVLTDHVVP LCLPERTFSE RTLAFVRFSL VSGWGQLLDR GATALELMVL
301  NVPRLMTQDC LQQSRKVGDS PNITEYMFCA GYSDGSKDSC KGDSGGPHAT HYRGTWYLTG
361  IVSWGQGCAT VGHFGVYTRV SQYIEWLQKL MRSEPRPGVL LRAPFP (SEQ ID NO: 2)
```

Figure 10B

Protein C Zymogen

```
1    MWQLTSLLLF VATWGISGTP APLDSVFSSS ERAHQVLRIR KRANSFLEEL RHSSLERECI
61   EEICDFEEAK EIFQNVDDTL AFWSKHVDGD QCLVLPLEHP CASLCCGHGT CIDGIGSFSC
121  DCRSGWEGRF CQREVSFLNC SLDNGGCTHY CLEEVGWRRC SCAPGYKLGD DLLQCHPAVK
181  FPCGRPWKRM EKKRSHLKRD TEDQEDQVDP RLIDGKMTRR GDSPWQVVLL DSKKKLACGA
241  VLIHPSWVLT AAHCMDESKK LLVRLGEYDL RRWEKWELDL DIKEVFVHPN YSKSTTDNDI
301  ALLHLAQPAT LSQTIVPICL PDSGLAEREL NQAGQETLVT GWGYHSSREK EAKRNRTFVL
361  NFIKIPVVPH NECSEVMSNM VSENMLCAGI LGDRQDACEG DSGGPMVASF HGTWFLVGLV
421  SWGEGCGLLH NYGVYTKVSR YLDWIHGHIR DKEAPQKSWA P (SEQ ID NO: 3)
```

Figure 10C

Protein C

```
1    ANSFLEELRH SSLERECIEE ICDFEEAKEI FQNVDDTLAF WSKHVDGDQC LVLPLEHPCA
61   SLCCGHGTCI DGIGSFSCDC RSGWEGRFCQ REVSFLNCSL DNGGCTHYCL EEVGWRRCSC
121  APGYKLGDDL LQCHPAVKFP CGRPWKRMEK KRSHLKRDTE DQEDQVDPRL IDGKMTRRGD
181  SPWQVVLLDS KKKLACGAVL IHPSWVLTAA HCMDESKKLL VRLGEYDLRR WEKWELDLDI
241  KEVFVHPNYS KSTTDNDIAL LHLAQPATLS QTIVPICLPD SGLAERELNQ AGQETLVTGW
301  GYHSSREKEA KRNRTFVLNF IKIPVVPHNE CSEVMSNMVS ENMLCAGILG DRQDACEGDS
361  GGPMVASFHG TWFLVGLVSW GEGCGLLHNY GVYTKVSRYL DWIHGHIRDK EAPQKSWAP
     (SEQ ID NO: 4)
```

Figure 10D $PC_{gla-egf1}$FVII Zymogen

```
1    MWQLTSLLLF VATWGISGTP APLDSVFSSS ERAHQVLRIR KRANSFLEEL RHSSLERECI
61   EEICDFEEAK EIFQNVDDTL AFWSKHVDGD QCLVLPLEHP CASLCCGHGT CIDGIGSFSC
121  DCRSGWEGRF CQRKDDQLIC VNENGGCEQY CSDHTGTKRS CRCHEGYSLL ADGVSCTPTV
181  EYPCGKIPIL EKRNASKPQG RIVGGKVCPK GECPWQVLLL VNGAQLCGGT LINTIWVVSA
241  AHCFDKIKNW RNLIAVLGEH DLSEHDGDEQ SRRVAQVIIP STYVPGTTNH DIALLRLHQP
301  VVLTDHVVPL CLPERTFSER TLAFVRFSLV SGWGQLLDRG ATALELMVLN VPRLMTQDCL
361  QQSRKVGDSP NITEYMFCAG YSDGSKDSCK GDSGGPHATH YRGTWYLTGI VSWGQGCATV
421  GHFGVYTRVS QYIEWLQKLM RSEPRPGVLL RAPFP (SEQ ID NO: 5)
```

Figure 10E $PC_{gla-egf1}$FVIIa

```
1    ANSFLEELRH SSLERECIEE ICDFEEAKEI FQNVDDTLAF WSKHVDGDQC LVLPLEHPCA
61   SLCCGHGTCI DGIGSFSCDC RSGWEGRFCQ RKDDQLICVN ENGGCEQYCS DHTGTKRSCR
121  CHEGYSLLAD GVSCTPTVEY PCGKIPILEK RNASKPQGRI VGGKVCPKGE CPWQVLLLVN
181  GAQLCGGTLI NTIWVVSAAH CFDKIKNWRN LIAVLGEHDL SEHDGDEQSR RVAQVIIPST
241  YVPGTTNHDI ALLRLHQPVV LTDHVVPLCL PERTFSERTL AFVRFSLVSG WGQLLDRGAT
301  ALELMVLNVP RLMTQDCLQQ SRKVGDSPNI TEYMFCAGYS DGSKDSCKGD SGGPHATHYR
361  GTWYLTGIVS WGQGCATVGH FGVYTRVSQY IEWLQKLMRS EPRPGVLLRA PFP
     (SEQ ID NO: 6)
```

Figure 10F

PC_{gla-egf1}FVII gtggaattcatgtggcagctcacaagcctcctgctgttcgtggccacctggggaatttccggcacaccag
ctcctcttgactcagtgttctccagcagcgagcgtgcccaccaggtgctgcggatccgcaaacgtgccaa
ctccttcctggaggagctccgtcacagcagcctggagcgggagtgcatagaggagatctgtgacttcgag
gaggccaaggaaattttccaaaatgtggatgacacactggccttctggtccaagcacgtcgacggtgacc
agtgcttggtcttgcccttggagcacccgtgcgccagcctgtgctgcgggcacggcacgtgcatcgacgg
catcggcagcttcagctgcgactgccgcagcggctgggagggccgcttctgccagcgcaaggatgaccag
ctgatctgtgtgaacgagaacggcggctgtgagcagtactgcagtgaccacacgggcaccaagcgctcct
gtcggtgccacgaggggtactctctgctggcagacggggtgtcctgcacacccacagttgaatatccatg
tggaaaaatacctattctagaaaaaagaaatgccagcaaaccccaaggccgaattgtgggggcaaggtg
tgccccaaggggagtgtccatggcaggtcctgttgttggtgaatggagctcagttgtgtgggggaccc
tgatcaacaccatctgggtggtctccgcggcccactgtttcgacaaaatcaagaactggaggaacctgat
cgcggtgctgggcgagcacgacctcagcgagcacgacggggatgagcagagccggcgggtggcgcaggtc
atcatccccagcacgtacgtcccgggcaccaccaaccacgacatcgcgctgctccgcctgcaccagcccg
tggtcctcactgaccatgtggtgcccctctgcctgcccgaacggacgttctctgagaggacgctggcctt
cgtgcgcttctcattggtcagcggctggggccagctgctggaccgtggcgccacggccctggagctcatg
gtcctcaacgtgccccggctgatgacccaggactgcctgcagcagtcacggaaggtgggagactccccaa
atatcacggagtacatgttctgtgccggctactcggatggcagcaaggactcctgcaaggggacagtgg
aggcccacatgccacccactaccggggcacgtggtacctgacgggcatcgtcagctggggccagggctgc
gcaaccgtgggccactttggggtgtacaccagggtctcccagtacatcgagtggctgcaaaagctcatgc
gctcagagccacgcccaggagtcctcctgcgagccccatttccctagctcgagtct (SEQ ID NO:7)

Figure 10G

PROTEIN C-FACTOR VII CHIMERAS

CROSS-REFERENCE TO RELATED APPLICATIONS

This application is U.S. national phase application under 35 U.S.C. § 371 of International Application No. PCT/US2019/045018, filed on Aug. 3, 2019, which claims the benefit of priority to U.S. Provisional Patent Application No. 62/714,189, filed on Aug. 3, 2018, the entire contents of each of which are hereby incorporated by reference in their entirety.

BACKGROUND

Blood coagulation factor VII (FVII) is a glycoprotein that is found in normal human plasma. When vascular injury occurs, trace amounts of the activated form of FVII (FVIIa) bind to an endothelial cell transmembrane receptor, tissue factor (TF), that becomes exposed at the site of injury. Under physiological conditions, TF-bound FVIIa (TF:FVIIa) rapidly activates blood coagulation Factor X (FX) leading to amplification of the intrinsic blood coagulation pathway for effective fibrin clot formation and hemostasis. Under pathological conditions, TF binding to FVIIa can lead to excessive fibrin clot formation and life-threatening thrombosis.

Within the vasculature, FVII/FVIIa is known to bind to a transmembrane receptor, endothelial cell Protein C receptor (EPCR), the primary receptor for Protein C (PC) and its activated form (APC) (Fukudome et al., 1994). APC is a potent anticoagulant enzyme that proteolytically inactivates blood coagulation factors Va and VIIIa, thereby down-regulating thrombin generation and fibrin clot formation (Kisiel, 1979). Pharmacologically administered recombinant FVIIa (rFVIIa) competitively inhibits PC binding to EPCR and PC activation by thrombin:thrombomodulin (Ghosh et al., 2007) to reduce the anticoagulant effects of APC and thereby contribute to the hemostatic effectiveness of rFVIIa (Keshava et al., 2017).

Severe hemophilia A and B are characterized by spontaneous bleeding episodes, resulting in an overall mortality rate six times greater than the unaffected population. Because hemophilia is caused by a deficiency of critical coagulation factors, standard treatments rely on replacing the missing factor with recombinant or plasma-derived protein. Unfortunately, up to 33% of severe hemophilia patients develop neutralizing alloantibodies against these replacement factors, rendering them ineffective. Once the development of alloantibodies occurs, the treatment options for acute bleeding are extremely limited. Currently, the preferred treatment option involves the use of rFVIIa to bypass the missing factors by binding to platelets and activating Factor X directly on the platelet surface. However, the use of rFVIIa requires frequent high dosing at significant cost, and is limited by an inconsistent response with pronounced interpatient variability.

In 1998, it was speculated that rFVIIa might also be useful as a "universal" hemostatic agent in patients without blood coagulation defects, who were suffering from uncontrolled bleeding for reasons other than hemophilia, e.g., bleeding related to surgery or trauma (Hedner, 1998). In the years that have followed, there is evidence that rFVIIa may be effective in minimizing blood loss in a variety of clinical settings; however, the known risk of TF-driven thrombosis has been a strong deterrent for early intervention, and has led to the use of treatment regimens with limited dosages and frequency of administration. Metanalyses that have generally not considered these constraints have concluded that the use of rFVIIa to control bleeding is ineffective and unsafe in non-hemophilia patients (Yank et al., 2011).

There is a need to develop FVII variants that display reduced tissue factor-dependent thrombogenicity. Previous attempts to improve rFVIIa therapy have failed, in part, because the mechanism of platelet-rFVIIa binding is not well understood.

SUMMARY OF THE INVENTION

Some of the main aspects of the present invention are summarized below. Additional aspects are described in the Detailed Description of the Invention, Examples, Drawings, and Claims sections of this disclosure. The description in each section of this disclosure is intended to be read in conjunction with the other sections. Furthermore, the various embodiments described in each section of this disclosure can be combined in various different ways, and all such combinations are intended to fall within the scope of the present invention.

The therapeutic mechanism of action of rFVIIa has been shown to involve activated platelet binding, as opposed to TF binding (Monroe et al., 1997). We have recently discovered that human platelets express EPCR, suggesting that modulation of EPCR binding could be utilized to enhance the hemostatic efficacy of FVIIa variants (Fager et al. 2018). The present disclosure provides procoagulant PC-FVII chimeras that bind to EPCR on platelets and on endothelial cells, and display anti-inflammatory properties and endothelial cell barrier stabilization properties. In addition, the PC-FVII chimeras display no detectable binding to TF, leading to reduced TF-dependent thrombogenicity compared to wild-type or recombinant FVII.

In particular, the invention provides a chimeric PC-FVII protein comprising a Gla domain of PC, an EGF-1 domain of PC, an EGF-2 domain of FVII, and a protease domain of FVII. An exemplary chimeric PC-FVII protein of the invention has the amino acid sequence set forth in SEQ ID NO: 6 and is referred to herein as $PC_{gla\text{-}egf1}$FVIIa. The activated form of the chimeric PC-FVII proteins of the invention is a heterodimer.

Accordingly, in one form, the chimeric PC-FVII protein is comprised of a single amino acid chain. In another form, chimeric PC-FVII protein comprises (i) a light chain comprising a Gla domain from PC, an EGF-1domain from PC, and an EGF-2 domain from FVII; and (ii) a heavy chain comprising a protease domain from FVII. The light chain and the heavy chain are linked to one another, preferably by a disulfide bond. Other linkages can include, for example, salt bridges, ionic bonds, peptide linkers, and/or lactam bridges.

In one embodiment, the Gla domain comprises the amino acid sequence set forth in SEQ ID NO: 9. In one embodiment, the EGF-1 domain comprises the amino acid sequence set forth in SEQ ID NO: 12. In one embodiment, the EGF-2 domain comprises the amino acid sequence set forth in SEQ ID NO: 11. In one embodiment, the protease domain comprises the amino acid sequence set forth in SEQ ID NO: 14. In one embodiment, the protease domain comprises the amino acid sequence set forth in SEQ ID NO: 15.

In a particular embodiment, the invention provides a chimeric PC-FVII protein comprising the amino acid sequence set forth in SEQ ID NO: 6.

In some embodiments, the chimeric PC-FVII protein of the invention comprises a propeptide sequence, wherein the propeptide sequence is capable of binding vitamin K-dependent γ-glutamyl carboxylase. In some embodiments, the chimeric PC-FVII protein further comprises an endoplasmic reticulum translocalization signal peptide.

In a particular embodiment, the invention provides a chimeric PC-FVII protein comprising the amino acid sequence set forth in SEQ ID NO: 5.

A further aspect of the invention provides a composition comprising a chimeric PC-FVII protein of the invention. In one embodiment, the composition is a pharmaceutical composition.

An additional aspect of the invention provides a kit comprising a chimeric PC-FVII protein or a composition of the invention. In one embodiment, the composition is contained in a pre-filled syringe.

The invention also provides a nucleic acid encoding a chimeric PC-FVII protein of the invention. In one embodiment, the nucleic acid comprises the nucleotide sequence set forth in SEQ ID NO: 7.

Also provided are chimeric PC-FVII proteins and compositions of the invention for use in activating Factor X (FX), and a method of activating FX. The method comprises contacting FX with an activated chimeric PC-FVII protein of the invention, wherein the chimeric PC-FVII protein cleaves FX, thereby producing activated Factor X (FXa). In one embodiment, the method is performed in the absence of TF. In one embodiment the method is performed in blood or plasma. In a particular embodiment, activating FX by contacting it with a chimeric PC-FVII protein results in increased thrombin concentration in the blood or plasma, compared to contacting FX with wild-type or recombinant FVIIa. In certain embodiments, the methods and uses of the invention are performed in vitro or ex vivo.

BRIEF DESCRIPTION OF THE DRAWINGS

The $PC_{gla-egf1}$FVIIa chimera contains the protease and EGF-2 domains of Factor VIIa (FVIIa) with the EGF-1 and Gla domains of Protein C (PC). FIG. 1A shows a ribbon diagram of the predicted structure of $PC_{gla-egf1}$FVIIa, based on the crystal structures of FVIIa and PC. FIG. 1B shows the unactivated or zymogen form of $PC_{gla-egf1}$FVII (PC-FVII), which is in the form of a single-chain polypeptide. The single-chain zymogen is converted into a two-chain, disulfide bond-linked, activated form of PC-FVII (PC-FVIIa) by proteolytic cleavage of the Arg159-Ile160 peptide bond (FIG. 1C).

FIG. 6A shows phospholipid vesicles (40 μM) incubated with 20 nM rFVIIa (●), $PC_{gla-egf1}$FVIIa (■), or $FIX_{gla-egf1}$FVIIa (▲). Plasma levels (135 nM) of FX were added and FXa generation was assessed by continuously monitoring cleavage of a chromogenic substrate (Pefachrome Xa). Data shown are actual FXa generation rates as a function of absorbance at 405 nm over time. FIG. 6B shows linear rates of FXa generation (mOD/min), calculated from the data shown in FIG. 6A.

FIG. 7A shows TF-dependent activity, assessed by incubating varying amounts of rFVIIa (0-2000 pM) (●), 2000 pM $PC_{gla-egf1}$FVIIa (■), 2000 pM $FIX_{gla-egf1}$FVIIa (♦), or vehicle control (▲) with 1 nM TF (Innovin). Plasma levels (135 nM) of FX were added and FXa generation was assessed by continuously monitoring cleavage of a chromogenic substrate (Pefachrome Xa). Data shown are actual FXa generation rates as a function of absorbance at 405 nm over time. FIG. 7B shows linear rates of FXa generation (mOD/min), calculated for each molecule from the data shown in FIG. 7A. The lack of FX activation, even at 100-fold higher concentration than that of rFVIIa, confirms that the interaction between TF and these chimeras is significantly reduced.

FIGS. 10A-10F show the amino acid sequences of human FVII zymogen (FIG. 10A; SEQ ID NO: 1); human FVII (FIG. 10B; SEQ ID NO: 2); human PC zymogen (FIG. 10C; SEQ ID NO: 3); human PC (FIG. 10D; SEQ ID NO: 4); a PC-FVII chimeric zymogen of the invention (FIG. 10E; SEQ ID NO: 5); a PC-FVII chimera of the invention, $PC_{gla-egf1}FVIIa$ (FIG. 10F; SEQ ID NO: 6); and a cDNA sequence encoding the $PC_{gla-egf1}FVII$ zymogen (FIG. 10G; SEQ ID NO: 7), including cloning sites. The bolded residues in FIG. 10E and FIG. 10F indicate amino acid sequences from PC. The italicized residues in FIG. 10E and FIG. 10F indicate amino acid sequences from FVII. The bolded, italicized, underlined residues in FIG. 10E and FIG. 10F indicate the FVII activation site; cleavage of the peptide bond between these two residues produces a light chain and heavy chain, which remain linked by a disulfide bond, activating the molecule. The bolded, underlined nucleotides in FIG. 10G indicate the start and stop codons.

DETAILED DESCRIPTION OF THE INVENTION

Figure 1A:
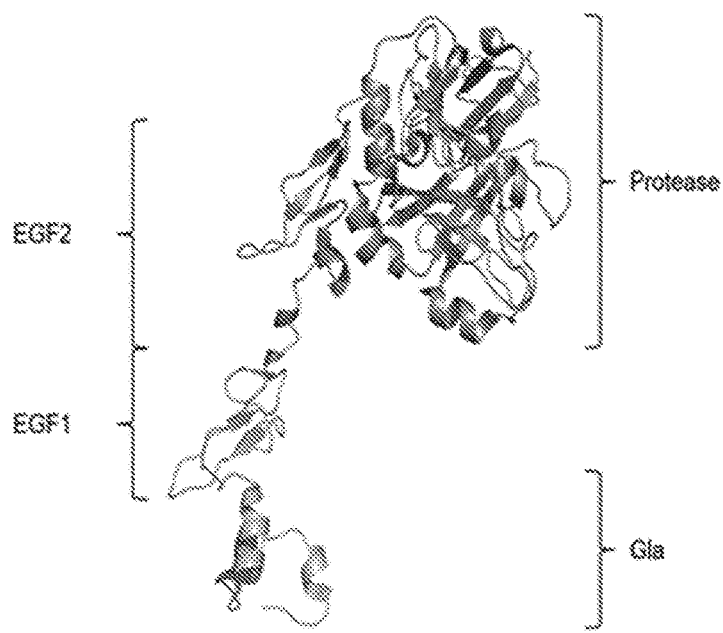
FIGS. 1A-1C show the structure of a representative chimera of the invention.
Figure 1B:
Figure 1C:
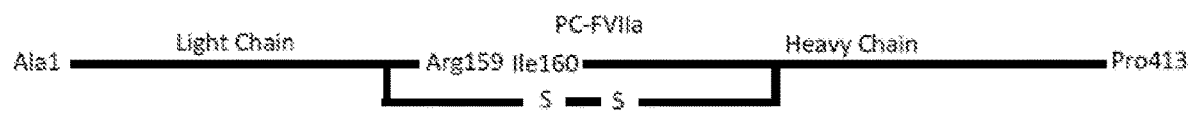
Figure 2:
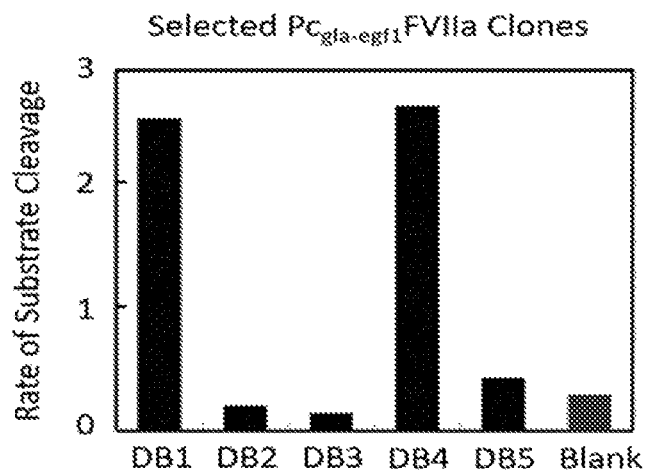
FIG. 2 shows screening of the initial chimera clones. Media from five separate $PC_{gla-egf1}$FVIIa clones (DB1-5) was assayed for activity by monitoring the cleavage of a FVIIa chromogenic substrate. Activity was compared to media from a cell-free well (blank).
Figure 3:
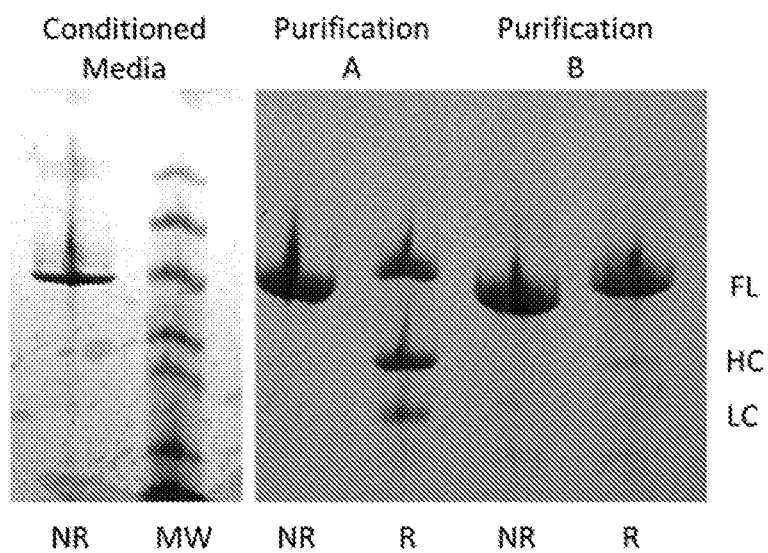
FIG. 3 shows gel electrophoresis of purified $PC_{gla-egf1}$FVIIa. The chimera was isolated from conditioned media of clones expressing significant FVIIa activity. The starting media (lane 1) and eluates from two separate purifications A (lanes 3-4) and B (lanes 5-6) were subjected to SDS-PAGE under reducing (R) and non-reducing (NR) conditions as shown. Full length (FL) chimera is seen for all purifications. The samples from purification A are partially activated as evidenced by the presence of both Heavy Chain (HC) and Light Chain (LC) portions under reducing conditions. Molecular weight markers (MW) are shown in lane 2.
Figure 4:
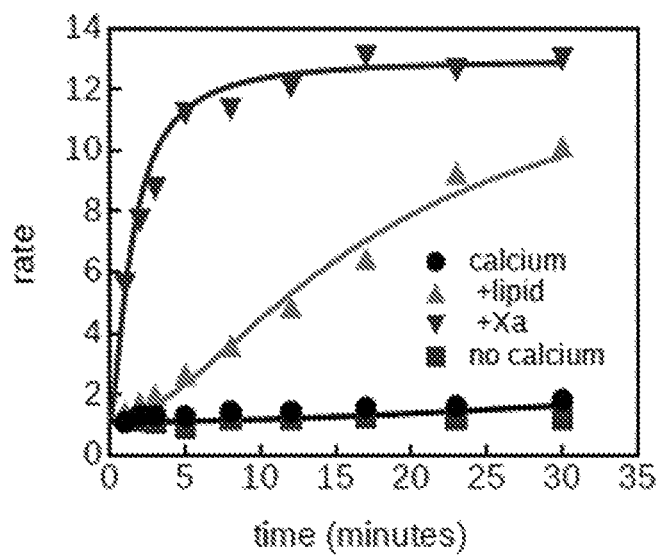
FIG. 4 shows $PC_{gla-egf1}$FVIIa autoactivation. Purified $PC_{gla-egf1}$FVIIa (2 μM) was incubated for varying amounts of time in the absence of calcium (■) prior to determining the amount of autoactivated chimera as evidenced by its ability to cleave a FVIIa substrate. The amount of autoactivation was compared to chimera incubated in the presence of calcium (5 mM) either with (▲) or without (●) phospholipid (100 μM). The rate of autoactivation was also compared to the rate of activation by 20 nM FXa in the presence of both calcium and phospholipid (▼). Rates are expressed as absorbance change per minute (mOD/min).

The practice of the present invention will employ, unless otherwise indicated, conventional techniques of pharmaceutics, formulation science, protein chemistry, cell biology, cell culture, molecular biology, microbiology, recombinant DNA, and immunology, which are within the skill of the art.

In order that the present invention can be more readily understood, certain terms are first defined. Additional definitions are set forth throughout the disclosure. Unless defined otherwise, all technical and scientific terms used herein have the same meaning as commonly understood by one of ordinary skill in the art to which this invention is related.

Any headings provided herein are not limitations of the various aspects or embodiments of the invention, which can be had by reference to the specification as a whole. Accordingly, the terms defined immediately below are more fully defined by reference to the specification in its entirety.

All references cited in this disclosure are hereby incorporated by reference in their entireties. In addition, any manufacturers' instructions or catalogues for any products cited or mentioned herein are incorporated by reference. Documents incorporated by reference into this text, or any teachings therein, can be used in the practice of the present invention. Documents incorporated by reference into this text are not admitted to be prior art.

I. Definitions

The phraseology or terminology in this disclosure is for the purpose of description and not of limitation, such that the terminology or phraseology of the present specification is to be interpreted by the skilled artisan in light of the teachings and guidance.

As used in this specification and the appended claims, the singular forms "a," "an," and "the" include plural referents, unless the context clearly dictates otherwise. The terms "a" (or "an") as well as the terms "one or more" and "at least one" can be used interchangeably.

Furthermore, "and/or" is to be taken as specific disclosure of each of the two specified features or components with or without the other. Thus, the term "and/or" as used in a phrase such as "A and/or B" is intended to include A and B, A or B, A (alone), and B (alone). Likewise, the term "and/or" as used in a phrase such as "A, B, and/or C" is intended to include A, B, and C; A, B, or C; A or B; A or C; B or C; A and B; A and C; B and C; A (alone); B (alone); and C (alone).

Wherever embodiments are described with the language "comprising," otherwise analogous embodiments described in terms of "consisting of" and/or "consisting essentially of" are included.

Units, prefixes, and symbols are denoted in their Système International de Unites (SI) accepted form. Numeric ranges are inclusive of the numbers defining the range, and any individual value provided herein can serve as an endpoint for a range that includes other individual values provided herein. For example, a set of values such as 1, 2, 3, 8, 9, and 10 is also a disclosure of a range of numbers from 1-10, from 1-8, from 3-9, and so forth. Likewise, a disclosed range is a disclosure of each individual value encompassed by the range. For example, a stated range of 5-10 is also a disclosure of 5, 6, 7, 8, 9, and 10.

The terms "polypeptide," "peptide," and "protein" are used interchangeably herein to refer to polymers of amino acids of any length. The polymer can be linear or branched, can comprise modified amino acids, and can be interrupted by non-amino acids. Except where indicated otherwise, e.g., for the abbreviations for the uncommon or unnatural amino acids set forth herein, the three-letter and one-letter abbreviations, as used in the art, are used herein to represent amino acid residues. Except where specifically indicated, peptides are indicated with the N-terminus of the left and the sequence is written from the N-terminus to the C-terminus.

Polypeptides, peptides, and proteins can comprise natural or synthetic post-translational modifications, for example, disulfide bonds, lactam bridges, carboxylation, hydroxylation, glycosylation, lipidation, alkylation, acetylation, acylation, amidation, phosphorylation, or other manipulations or modification, such as conjugation with a labeling component or addition of a protecting group. Also included are, for example, polypeptides containing one or more analogs of an amino acid (including, for example, amino-isobutyric acid (Aib), unnatural amino acids, such as naphthylalanine (Nal), etc.), as well as other modifications known in the art. In certain embodiments, the polypeptides can occur as single chains, covalent dimers, or non-covalent associated chains.

A "chimera" or "chimeric" molecule is one comprising structural features of more than one reference molecule. In the context of the present invention, a chimeric protein comprises an amino acid sequence from a first polypeptide and an amino acid sequence from a second polypeptide. The amino acid sequences can be linked covalently, such as, for example, by peptide bonds or disulfide bonds. The amino acid sequences can be contiguous, i.e., directly fused, or can comprise a linker, such as a peptide linker, between the amino acid sequence from a first polypeptide and the amino acid sequence of a second polypeptide.

The term "coagulation factor" refers to a protein involved in the coagulation cascade, in either its activated or zymogen form. Coagulation factors include serine proteases, such as Factor VII, Factor IX, Factor X, Factor XI, Factor XII, prothrombin, and Protein C; glycoproteins, such as Factor V, Factor VIII, and protein S; and transglutaminases, such as Factor XIII.

The term "variant" refers to a peptide having one or more amino acid substitutions, deletions, and/or insertions compared to a reference sequence. Deletions and insertions can be internal and/or at one or more termini.

The term "conservative substitution" as used herein denotes that one or more amino acids are replaced by another, biologically similar residue. Examples include substitution of amino acid residues with similar characteristics, e.g., small amino acids, acidic amino acids, polar amino acids, basic amino acids, hydrophobic amino acids, and aromatic amino acids. For further information concerning phenotypically silent substitutions in peptides and proteins, see, for example, Bowie et. al., *Science* 247:1306-1310 (1990). In Table I, conservative substitutions of amino acids are grouped by physicochemical properties; I: neutral and/or hydrophilic, II: acids and amides, III: basic, IV: hydrophobic, V: aromatic, bulky amino acids.

TABLE I

| I | II | III | IV | V |
|---|----|-----|----|---|
| A | N  | H   | M  | F |
| S | D  | R   | L  | Y |
| T | E  | K   | I  | W |
| P | Q  |     | V  |   |
| G |    |     | C  |   |

In Table II, conservative substitutions of amino acids are grouped by physicochemical properties; VI: neutral or hydrophobic, VII: acidic, VIII: basic, IX: polar, X: aromatic.

TABLE II

| VI | VII | VIII | IX | X |
|----|-----|------|----|---|
| A  | D   | H    | M  | F |
| L  | E   | R    | S  | Y |
| I  |     | K    | T  | W |
| V  |     |      | N  | H |
| P  |     |      | Q  |   |
| G  |     |      | C  |   |

Methods of identifying conservative nucleotide and amino acid substitutions which do not affect protein function are well-known in the art (see, e.g., Brummell et al., *Biochem.* 32:1180-1187 (1993); Kobayashi et al., *Protein Eng.* 12(10):879-884 (1999); and Burks et al., *Proc. Natl. Acad. Sci. U.S.A.* 94:412-417 (1997)).

The terms "identical" or percent "identity" in the context of two or more nucleic acids or peptides, refers to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms, or by visual inspection. Various algorithms and software are known in the art that can be used to obtain alignments of amino acid or nucleotide sequences.

One such non-limiting example of a sequence alignment algorithm is described in Karlin et al., *Proc. Natl. Acad. Sci.*, 87:2264-2268 (1990), as modified in Karlin et al., *Proc. Natl. Acad. Sci.*, 90:5873-5877 (1993), and incorporated into the NBLAST and XBLAST programs (Altschul et al., *Nucleic Acids Res.*, 25:3389-3402 (1991)). In certain embodiments, Gapped BLAST can be used as described in Altschul et al., *Nucleic Acids Res.* 25:3389-3402 (1997).

BLAST-2, WU-BLAST-2 (Altschul et al., *Methods in Enzymology*, 266:460-480 (1996)), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in the GCG software package (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* (48):444-453 (1970)), can be used to determine the percent identity between two amino acid sequences (e.g., using either a BLOSUM 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (*CABIOS* 4:11-17 (1989)). For example, the percent identity can be determined using the ALIGN program (version 2.0) and using a PAM120 with residue table, a gap length penalty of 12 and a gap penalty of 4. One skilled in the art can determine appropriate parameters for maximal alignment by particular alignment software. In certain embodiments, the default parameters of the alignment software are used. Other resources for calculating identity include methods described in *Computational Molecular Biology* (Lesk ed., 1988); *Biocomputing: Informatics and Genome Projects* (Smith ed., 1993); *Computer Analysis of Sequence Data, Part 1* (Griffin and Griffin eds., 1994); *Sequence Analysis in Molecular Biology* (G. von Heinje, 1987); *Sequence Analysis Primer* (Gribskov et al. eds., 1991); and Carillo et al., *SIAM J. Applied Math.*, 48:1073 (1988).

A "polynucleotide," as used herein can include one or more "nucleic acids," "nucleic acid molecules," or "nucleic acid sequences," and refers to a polymer of nucleotides of any length, and includes DNA and RNA. The polynucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. The preceding description applies to all polynucleotides referred to herein, including RNA and DNA.

An "isolated" molecule is one that is in a form not found in nature, including those which have been purified.

A "label" is a detectable compound that can be conjugated directly or indirectly to a molecule, so as to generate a "labeled" molecule. The label can be detectable on its own (e.g., radioisotope labels or fluorescent labels), or can be indirectly detected, for example, by catalyzing chemical alteration of a substrate compound or composition that is detectable (e.g., an enzymatic label) or by other means of indirect detection (e.g., biotinylation).

"Binding affinity" generally refers to the strength of the sum total of non-covalent interactions between a single binding site of a molecule and its binding partner (e.g., a receptor and its ligand, an antibody and its antigen, two monomers that form a dimer, etc.). Unless indicated otherwise, as used herein, "binding affinity" refers to intrinsic binding affinity which reflects a 1:1 interaction between members of a binding pair. The affinity of a molecule X for its partner Y can generally be represented by the dissociation constant ($K_D$). Affinity can be measured by common methods known in the art, including those described herein. Low-affinity binding partners generally bind slowly and tend to dissociate readily, whereas high-affinity binding partners generally bind faster and tend to remain bound longer.

The affinity or avidity of a molecule for its binding partner can be determined experimentally using any suitable method known in the art, e.g., flow cytometry, enzyme-linked immunosorbent assay (ELISA), or radioimmunoassay (MA), or kinetics (e.g., KINEXA® or BIACORE™ or OCTET® analysis). Direct binding assays as well as competitive binding assay formats can be readily employed. (See, e.g., Berzofsky et al., "Antibody-Antigen Interactions," in *Fundamental Immunology*, Paul, W. E., ed., Raven Press: New York, N.Y. (1984); Kuby, *Immunology*, W. H. Freeman and Company: New York, N.Y. (1992)). The measured affinity of a particular binding pair interaction can vary if measured under different conditions (e.g., salt concentration, pH, temperature). Thus, measurements of affinity and other binding parameters (e.g., $K_D$ or Kd, $K_{on}$, $K_{off}$) are made with standardized solutions of binding partners and a standardized buffer, as known in the art.

An "active agent" is an ingredient that is intended to furnish biological activity. The active agent can be in association with one or more other ingredients.

An "effective amount" of an active agent is an amount sufficient to carry out a specifically stated purpose.

The term "pharmaceutical composition" refers to a preparation that is in such form as to permit the biological activity of the active ingredient to be effective and which contains no additional components that are unacceptably toxic to a subject to which the composition would be administered. Such composition can be sterile and can comprise a pharmaceutically acceptable carrier, such as physiological saline. Suitable pharmaceutical compositions can comprise one or more of a buffer, a surfactant, a stabilizing agent, a preservative, and/or other conventional solubilizing or dispersing agents.

The terms "inhibit," "block," and "suppress" are used interchangeably and refer to any statistically significant decrease in occurrence or activity, including full blocking of the occurrence or activity. For example, "inhibition" can refer to a decrease of about 10%, 20%, 30%, 40%, 50%, 60%, 70%, 80%, 90% or 100% in activity or occurrence. An "inhibitor" is a molecule, factor, or substance that produces a statistically significant decrease in the occurrence or activity of a process, pathway, or molecule.

II. Protein C-Factor VII Chimeras

Blood coagulation factors activated Factor VII (FVIIa) and Activated Protein C (APC) are vitamin K-dependent, glycosylated, heterodimeric serine proteases, each derived from a zymogen precursor. The canonical amino acid sequence of the human FVII zymogen is set forth in GenBank Accession No. AAA88040 and in FIG. 10A; that of human PC is set forth in GenBank Accession No. P04070 and in FIG. 10C. A number of natural variants of each protein have been identified (see, e.g., UniProtKB Entry P08709; UniProtKB Entry P04070). Sequences from such variants are suitable for use in the PC-FVII chimeras of the invention.

Mature FVIIa contains 406 amino acids and results from a single proteolytic cleavage between amino acids R152 and 1153 of FVII; the N-terminal signal peptide and propeptide are also cleaved (e.g., SEQ ID NO: 2; FIG. 10B). Following cleavage of its signal peptide and propeptide sequences, PC contains 419 amino acids (e.g., SEQ ID NO: 4; FIG. 10D).

FVIIa and PC share a similar molecular structure with other coagulation serine proteases (e.g., Factor IXa and Factor Xa), each having a light chain and a heavy chain. The light chain is comprised of an amino terminal gamma-carboxyglutamic acid (Gla) domain and two epidermal growth factor (EGF)-like domains, while the heavy chain is comprised of a protease domain (see Lazarus et al., 2004).

A "Gla domain" is an amino acid sequence from a coagulation factor, which amino acid sequence binds directly to phospholipid membranes. The Gla domains of FVII/FVIIa and PC can also bind to phospholipid membranes via the transmembrane endothelial cell Protein C receptor (EPCR) (see Ghosh et al., 2007). PC binding to EPCR promotes PC activation by the thrombin:thrombomodulin complex. The Gla domain of FVII/FVIIa can comprise, for example, amino acids from about position 1 to about position 45 of SEQ ID NO: 2 (SEQ ID NO: 8). The Gla domain of PC can comprise, for example amino acids from about position 1 to about position 46 of SEQ ID NO: 4 (SEQ ID NO: 9). The Gla domain can include post-translational modifications, for example, carboxylation, such as γ-carboxylation, and/or hydroxylation, such as β-hydroxylation.

An "EGF domain" is a cysteine-rich amino acid sequence, typically about 30-45 residues in length, found originally in epidermal growth factor. A range of proteins involved in cell signaling and in the coagulation cascade contain EGF domains. The EGF domains of FVIIa and PC are involved in cofactor recognition. For example, the EGF-1 domain of FVIIa plays a critical role in its affinity for TF. The EGF-1 domain of PC, on the other hand, is not known to have an affinity for TF. The EGF-1 domain of FVII/FVIIa can comprise, for example, amino acids from about position 46 to about position 82 of SEQ ID NO: 2 (SEQ ID NO: 10). The EGF-2 domain of FVII/FVIIa can comprise, for example, amino acids from about position 87 to about position 128 of SEQ ID NO: 2 (SEQ ID NO: 11). The EGF-1 domain of PC can comprise, for example, amino acids from about position 55 to about position 90 of SEQ ID NO: 4 (SEQ ID NO: 12). The EGF-2 domain of PC can comprise, for example, amino acids from about position 94 to about position 134 of SEQ ID NO: 4 (SEQ ID NO: 13). Each EGF domain can include post-translational modifications, for example, hydroxylation, such as β-hydroxylation, and/or glycosylation, such as N-glycosylation and/or O-glycosylation and/or fucosylation.

The protease domain of FVIIa is responsible for its cleavage/activation of Factor IX and Factor X. Activated Protein C (APC) proteolytically inactivates Factor Va and Factor VIIIa to downregulate the process of blood coagulation, which has direct anti-coagulant, anti-hemostatic and/or anti-thrombotic effects. FVIIa binding to EPCR can displace bound PC to competitively inhibit PC activation, which could have indirect pro-coagulant, pro-hemostatic and/or pro-thrombotic effects. The protease domain of FVII/FVIIa can comprise, for example, amino acids from about position 153 to about position 392 of SEQ ID NO: 2 (SEQ ID NO: 14), or from about position 153 to about position 406 of SEQ ID NO: 2 (SEQ ID NO: 15). The protease domain of PC can comprise, for example, amino acids from about position 169 to about position 408 of SEQ ID NO: 4 (SEQ ID NO: 16). The protease domain can include post-translational modifications, for example, phosphorylation and/or glycosylation, such as N-glycosylation.

The present inventors have discovered that chimeric PC-FVIIa comprising Gla and EGF1 domains from PC and EGF2 and protease domains from FVIIa has the membrane-binding and receptor-targeting properties of PC and the enzymatic activity of FVIIa, without the Tissue Factor (TF)

binding of FVIIa. The interaction between pharmacologically administered rFVIIa and TF is an established mechanism for thrombotic complications that have occurred in a clinical context. In their activated form, the PC-FVII chimeras of the invention can bind to EPCR on endothelial cells, which can cleave PAR1 and initiate intracellular signaling, leading to anti-inflammatory effects and preservation of the barrier function of endothelium.

Non-limiting examples of amino acid sequences that can be used in the invention are set forth in Table 1.

PC-FVII chimeras of the invention can optionally include one or more epitope and/or affinity tags, such as for purification or detection. Non-limiting examples of such tags include FLAG, HA, His, Myc, GST, and the like. PC-FVII chimeras of the invention can optionally include one or more labels.

In certain aspects, the invention provides a composition, e.g., a pharmaceutical composition, comprising a PC-FVII chimera of the invention, optionally further comprising one or more carriers, diluents, excipients, or other additives.

TABLE 1

| Domain | SEQ ID NO | Amino Acid Sequence |
|---|---|---|
| FVII Gla | 8 | ANAFLEELRPGSLERECKEEQCSFEEAREIFKDAERTKLFWISYS |
| PC Gla | 9 | ANSFLEELRHSSLERECIEEICDFEEAKEIFQNVDDTLAFWSKHVD |
| FVII EGF-1 | 10 | DGDQCASSPCQNGGSCKDQLQSYICFCLPAFEGRNCE |
| FVII EGF-2 | 11 | DQLICVNENGGCEQYCSDHTGTKRSCRCHEGYSLLADGVSCT |
| PC EGF-1 | 12 | LEHPCASLCCGHGTCIDGIGSFSCDCRSGWEGRFCQ |
| PC-EGF-2 | 13 | SFLNCSLDNGGCTHYCLEEVGWRRCSCAPGYKLGDDLLQCH |
| FVII Protease | 14 | IVGGKVCPKGECPWQVLLLVNGAQLCGGTLINTIWVVSAAHCFDKI<br>KNWRNLIAVLGEHDLSEHDGDEQSRRVAQVIIPSTYVPGTTNHDIA<br>LLRLHQPVVLTDHVVPLCLPERTFSERTLAFVRFSLVSGWGQLLDR<br>GATALELMVLNVPRLMTQDCLQQSRKVGDSPNITEYMFCAGYSDG<br>SKDSCKGDSGGPHATHYRGTWYLTGIVSWGQGCATVGHFGVYTR<br>VSQYIEWLQKLMR |
| FVII Protease | 15 | IVGGKVCPKGECPWQVLLLVNGAQLCGGTLINTIWVVSAAHCFDKI<br>KNWRNLIAVLGEHDLSEHDGDEQSRRVAQVIIPSTYVPGTTNHDIA<br>LLRLHQPVVLTDHVVPLCLPERTFSERTLAFVRFSLVSGWGQLLDR<br>GATALELMVLNVPRLMTQDCLQQSRKVGDSPNITEYMFCAGYSDG<br>SKDSCKGDSGGPHATHYRGTWYLTGIVSWGQGCATVGHFGVYTR<br>VSQYIEWLQKLMRSEPRPGVLLRAPFP |
| PC Protease | 16 | LIDGKMTRRGDSPWQVVLLDSKKKLACGAVLIHPSWVLTAAHCM<br>DESKKLLVRLGEYDLRRWEKWELDLDIKEVFVHPNYSKSTTDNDI<br>ALLHLAQPATLSQTIVPICLPDSGLAERELNQAGQETLVTGWGYHS<br>SREKEAKRNRTFVLNFIKIPVVPHNECSEVMSNMVSENMLCAGILG<br>DRQDACEGDSGGPMVASFHGTWFLVGLVSWGEGCGLLHNYGVYT<br>KVSRYLDWIHGHIR |

PC-FVII chimeras of the invention can include domains comprising more, fewer, or conservatively substituted amino acids compared with those sequences listed in Table 1, provided that the basic function of the domain is preserved. The chimeras can comprise solely wild-type FVII and PC amino acid sequences. Alternatively, the chimeras can comprise heterologous sequences (i.e., from neither wild-type FVII nor wild-type PC), for example, the chimeras can comprise one or more heterologous linkers between domains. The amino acid sequence of an exemplary PC-FVII chimera is shown in FIG. 10F.

PC-FVII chimeras of the invention can comprise a prepropeptide. The prepropeptide is typically comprised of a signal peptide, which directs localization of the molecule to the lumen of the endoplasmic reticulum, and a propeptide, which binds vitamin K-dependent γ-glutamyl carboxylase. The prepropeptide sequence can be from FVII, PC, or another coagulation factor, preferably from another vitamin K-dependent protein, for example, prothrombin, FIX, FX, Protein S, or Protein Z. The signal peptide and propeptide can be from the same or different proteins. Such signal and propeptide sequences are highly conserved and are known in the art (Kriegler et al., 2018; Stanley et al., 1999; Pan et al., 1985). The amino acid sequence of an exemplary PC-FVII chimera comprising a prepropeptide is shown in FIG. 10E.

Also within the scope of the invention are kits comprising the PC-FVII chimeras and compositions as provided herein and, optionally, instructions for use. In one embodiment, the kit comprises a syringe. The syringe can be pre-filled with a composition comprising a PC-FVII chimera of the invention. The kit can further contain at least one additional reagent, and/or one or more additional active agents. Kits typically include a label indicating the intended use of the contents of the kit. In this context, the term "label" includes any writing or recorded material supplied on or with the kit, or that otherwise accompanies the kit.

The PC-FVII chimeras can be used in various contexts, for example, as a model for studying coagulation, EPCR-mediated binding, and the effects of platelet vs. endothelial membrane microenvironment. PC-FVII chimera activity and function can be measured by known assays, including the assays described herein.

III. Methods of Preparation

PC-FVII chimeras of the invention can be chemically synthesized or can be expressed using recombinant methods. Synthesis or expression may occur as fragments of the protein which are subsequently combined either chemically or enzymatically.

Accordingly, also provided are nucleic acid molecules encoding PC-FVII chimeras of the invention. Nucleic acid molecules of the invention can be designed based on the amino acid sequence of the desired PC-FVII chimera and selection of those codons that are favored in the host cell in which the recombinant PC-FVII chimera will be produced. Standard methods can be applied to synthesize a nucleic acid molecule encoding a PC-FVII chimera of interest. An exemplary nucleotide sequence encoding a PC-FVII chimera of the invention is shown in FIG. 10G.

Once prepared, the nucleic acid encoding a particular PC-FVII chimera can be inserted into an expression vector and operably linked to an expression control sequence appropriate for expression of the peptide in a desired host. In order to obtain high expression levels of the PC-FVII chimera, the nucleic acid can be operably linked to or associated with transcriptional and translational expression control sequences that are functional in the chosen expression host.

A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from *E. coli*, including pCR1, pBR322, pMB9 and their derivatives, wider host range plasmids, such as *M*13, and filamentous single-stranded DNA phages.

Suitable host cells include prokaryotes, yeast, insect, or higher eukaryotic cells under the control of appropriate promoters. Prokaryotes include gram negative or gram positive organisms, for example *E. coli* or bacilli. Higher eukaryotic cells can be established or cell lines of mammalian origin, examples of which include *Pichia pastoris*, HEK293 cells, COS-7 cells, L cells, C127 cells, 3T3 cells, Chinese hamster ovary (CHO) cells, HeLa cells, and BHK cells. Cell-free translation systems can also be employed. Helper enzymes, such as vitamin K-dependent carboxylase (VKGC), vitamin K epoxide reductase (VKOR), and/or PACE/furin can be used to increase the levels of functional vitamin K-dependent protein expression.

DNA sequences for use in producing PC-FVII chimeras of the invention will typically encode a prepropeptide at the N-terminus to obtain proper post-translational processing and secretion from the host cell. As will be appreciate by those skilled in the art, additional modifications, such as amino acid additions, deletions, and substitutions, can be made in the amino acid sequence of the PC-FVII chimeras described herein, provided that those modifications do not significantly affect the protein's function.

EXAMPLES

Embodiments of the present disclosure can be further defined by reference to the following non-limiting examples. It will be apparent to those skilled in the art that many modifications, both to materials and methods, can be practiced without departing from the scope of the present disclosure. A number of variants to reference peptide ST-3 were made and examined, as described below.

Example 1. Expression and Purification of $PC_{gla\text{-}egf1}$FVIIa

We designed a chimeric cDNA encoding residues 1-91 (Gla and EGF1 domains) of human PC linked to residues 85-406 (EGF2 and Protease domains) of human FVIIa ($PC_{gla\text{-}egf1}$FVIIa) (FIG. 1). The cDNA encoding $PC_{gla\text{-}egf1}$FVIIa was synthesized and cloned into a pCDNA3.1(+) pCMV expression vector (OriGene). The vector was then stably transfected into human embryonic kidney (HEK293) cells (ATCC). Colonies were cloned into individual wells of a 24-well plate, and initial clones of interest were selected and screened (FIG. 2) for expression of the construct by monitoring cleavage of a chromogenic FVIIa substrate (Pentapharm). Briefly, conditioned media was collected and centrifuged to remove cell debris. The supernatant was concentrated using a Microcon-30 (Millipore Sigma) and activated by incubating with FXa (2 nM) and PS/41% PC/44% PE phospholipid vesicles (40 μM), in the presence of 3 mM $CaCl_2$ at RT for 30 minutes. Following activation, Rivaroxaban (4.75 mM) was added to inhibit residual FXa activity. Samples were incubated at RT for 5 min prior to adding 1 mM Pefachrome FVIIa. FVIIa activity was subsequently was assessed by continuously monitoring the cleavage of the chromogenic substrate at 405 nm every 12 seconds for 1 hour.

Candidate clones expressing significant FVIIa activity were expanded for purification of the chimera using sequential Q-Sepharose (GE Healthcare) and HiTrap S (GE Healthcare) columns eluted with a salt gradient as described (Chang et al., 1995). Two separate purifications (A and B) were completed using conditioned media from two separate clones. The eluates from each of the purification procedures were subjected to protein electrophoresis using 10-15% Phast gels (Pharmacia Biotech). The resulting bands are consistent with the expected molecular weight of $PC_{gla\text{-}egf1}$FVIIa (FIG. 3). Protein concentration was also determined using a BCA assay (Pierce).

Example 2. $PC_{gla\text{-}egf1}$FVIIa is Capable of Autoactivation

During the initial screens for chimera activity, the conditioned media from each candidate clone was purposefully activated by FXa as above to ensure activation of the chimera prior to screening for activity. However, protein electrophoresis of the eluate from the first purification procedure (FIG. 3 Purification A) showed that the chimera was isolated in a partially activated form even in the absence of pre-treatment with FXa. This same partial activation was not seen in the eluate from the second purification. Since FVIIa is capable of autoactivation, we evaluated the ability of the $PC_{gla\text{-}egf1}$FVIIa to autoactivate as well. For these experiments $PC_{gla\text{-}egf1}$FVIIa (2 μM) from the second purification was incubated with or without FXa (20 nM), $CaCl_2$ (5 mM), or phospholipid vesicles (100 μM). Following varying incubation periods (0-35 min), residual FXa and $CaCl_2$ were inhibited by adding Rivaroxaban (50 nM) and EDTA (5 mM). Pefachrome FVIIa (500 μm) was added and FVIIa activity was assessed by continuously monitoring the cleavage of the chromogenic substrate at 405 nm every 12 seconds for 30 min.

As shown in FIG. 4, autoactivation of the chimera occurs in the presence of calcium and phospholipid. However, autoactivation is significantly impaired in either the absence of calcium or in the presence of calcium without a phospholipid surface. As expected, the addition of FXa rapidly accelerates the activation of $PC_{gla\text{-}egf1}$FVIIa in the presence of calcium and phospholipid. Therefore, for experiments in which FXa cannot be added, (particularly those requiring measurement of FXa activity), the chimera can readily be activated by incubating with calcium and phospholipid.

Example 3. $PC_{gla-egf1}$FVIIa is Able to Cleave a Chromogenic FVIIa Substrate $FIX_{gla-egf1}$FVIIa is a chimera having the Gla and EGF1 domains of Factor IX and the EGF2 and protease domains of FVIIa (Chang et al., 1995). Antithrombin active-site titrations, as described (Grandoni et al., 2017), were performed to determine the relative protein concentration and enzymatic activity of $PC_{gla-egf1}$FVIIa and $FIX_{gla-egf1}$FVIIa in vitro. Since both contain the protease domain of FVIIa, $FIX_{gla-egf1}$FVIIa could be used as a positive control.

For these experiments 200 nM of either $PC_{gla-egf1}$FVIIa, $FIX_{gla-egf1}$FVIIa, or rFVIIa was incubated with 2.5 U/ml heparin and varying amounts (0-800 nM) of antithrombin for 14 hours at room temperature. Following incubation, 500 µM Pefachrome FVIIa was added and FVIIa activity was assessed by continuously monitoring the cleavage of this chromogenic substrate at 405 nm every 15 seconds for 10 min. The rate of substrate cleavage was then plotted against the original concentration of antithrombin in order to determine the concentration of active material in each sample.

Figure 5:
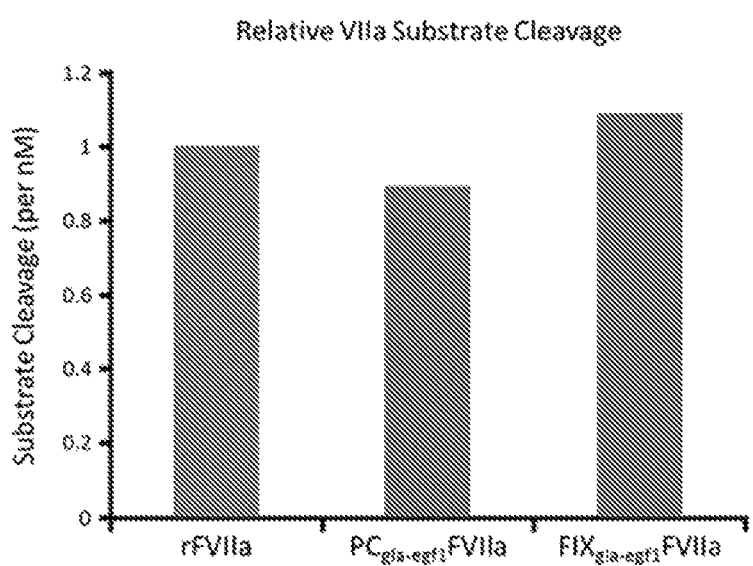
FIG. 5 shows that rFVIIa, $PC_{gla-egf1}$FVIIa, and $FIX_{gla-egf1}$FVIIa have similar rates of FVIIa substrate cleavage. Antithrombin was used for active-site titration to determine the relative protein concentration and activity of each molecule. 200 nM of either rFVIIa, $PC_{gla-egf1}$FVIIa, or $FIX_{gla-egf1}$FVIIa was incubated with 5 U/ml of heparin and varying amounts of antithrombin (0-800 nM) prior to adding a chromogenic substrate for FVIIa (Pefachrome VIIa, 500 FVIIa activity was assessed by continuously monitoring cleavage of the chromogenic substrate. Data shown are linear rates of FVIIa substrate cleavage per nM of enzyme.
Figure 6A:
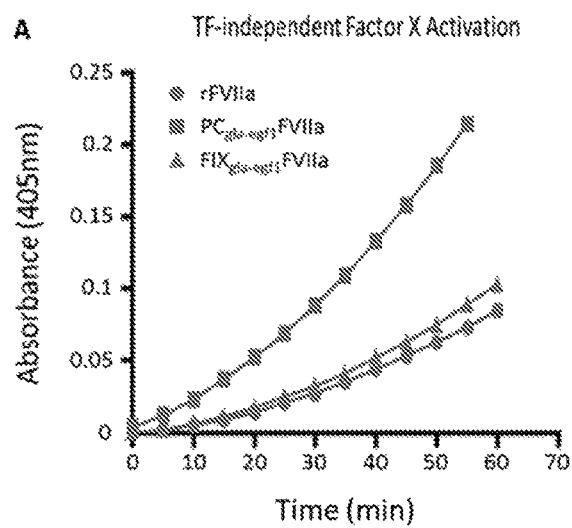
FIGS. 6A-6B show that Tissue Factor (TF)-independent activity of $PC_{gla-egf1}$FVIIa is increased compared to $FIX_{gla-egf1}$FVIIa and rFVIIa.
Figure 6B:
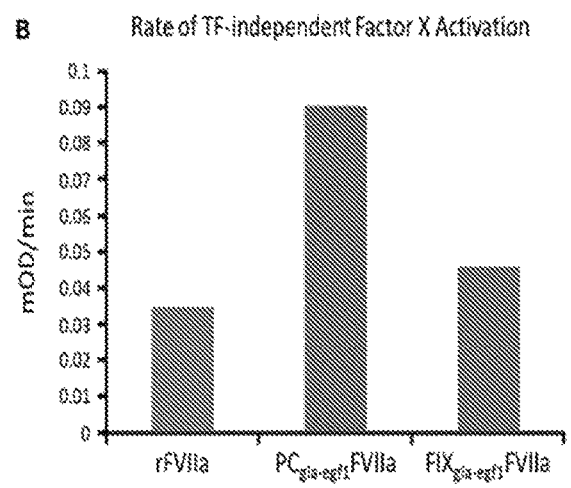
Figures 7A, 7B:
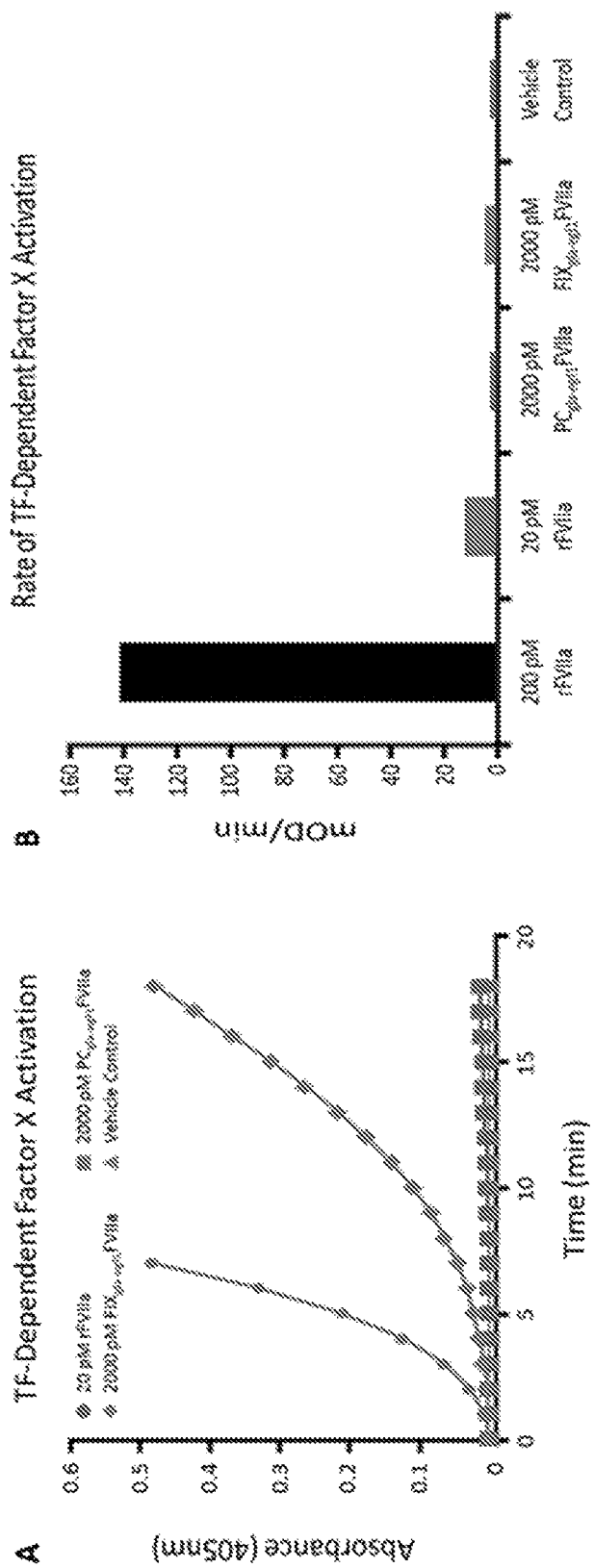
FIGS. 7A-7B show that $PC_{gla-egf1}$FVIIa has substantially reduced affinity for TF compared to rFVIIa.
Figure 8A:
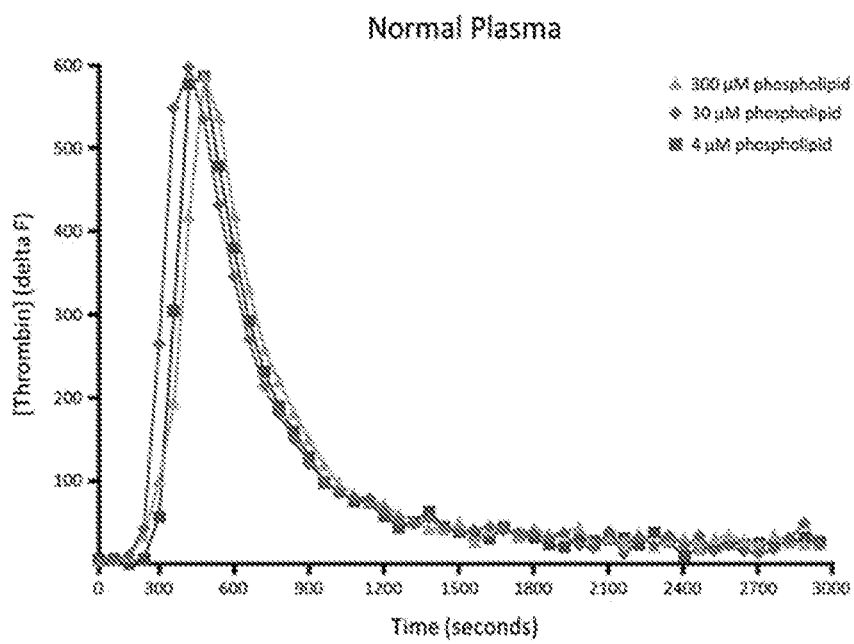
FIGS. 8A-8D show that $PC_{gla-egf1}$FVIIa and rFVIIa are sensitive to lipid concentration. Thrombin generation was assessed using a calibrated automated thrombography (CAT) assay. Hemophilia A (FVIII deficient) plasma was incubated either with (FIG. 8A) or without (FIG. 8B) 2 U/mL FVIII, followed by the addition of 1 pM TF and either 4 μM (■), 30 μM (♦), or 300 μM (▲) phospholipid vesicles in the presence of a fluorogenic thrombin substrate (432 μM). Thrombin generation was assessed by continuously monitoring the resulting change in fluorescence intensity as a result of substrate cleavage. Similar experiments were performed in Hemophilia A plasma following the addition of equal concentrations (20 μg/mL) of either rFVIIa (FIG. 8C) or $PC_{gla-egf1}$FVIIa (FIG. 8D). Data shown are actual thrombin generation rates as a function of the change in fluorescence intensity over time.
Figure 8B:
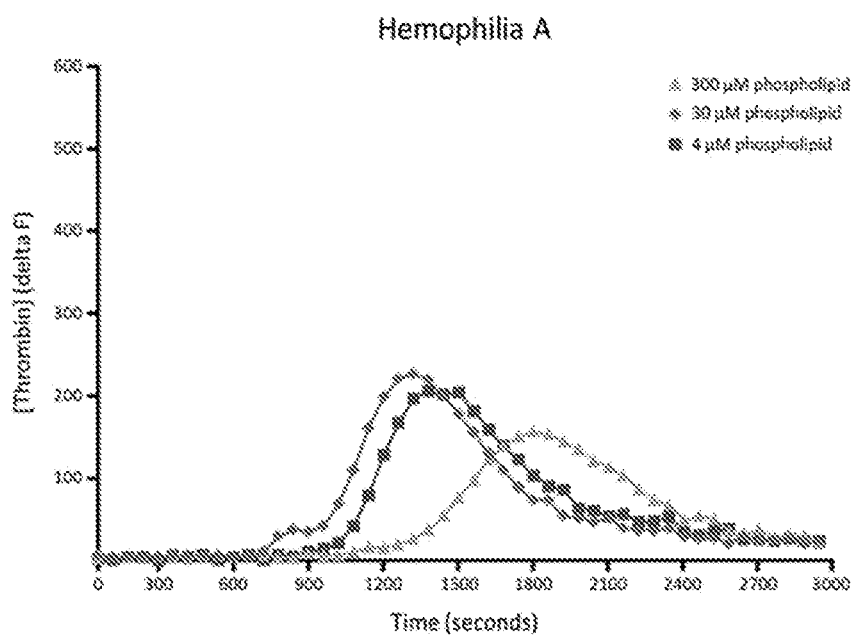
Figure 8C:
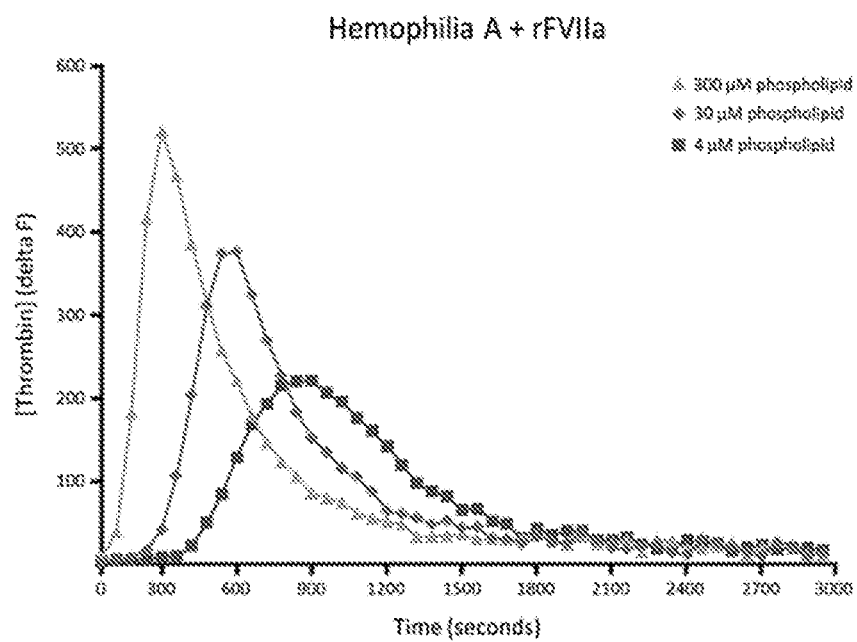
Figure 8D:
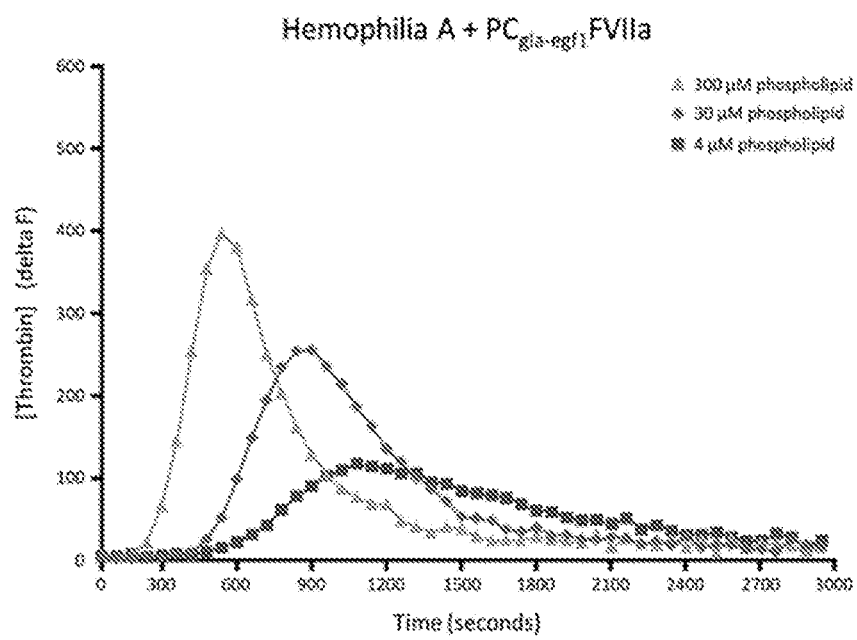

As shown in FIG. 5, both $PC_{gla-egf1}$FVIIa and $FIX_{gla-egf1}$FVIIa are able to cleave the synthetic FVIIa substrate. In addition, similar amounts of active protein resulted in similar rates of FVIIa substrate cleavage for all three molecules. This result confirms that the rate of substrate cleavage is a good indication of the number of active sites for each chimera.

Figure 9:
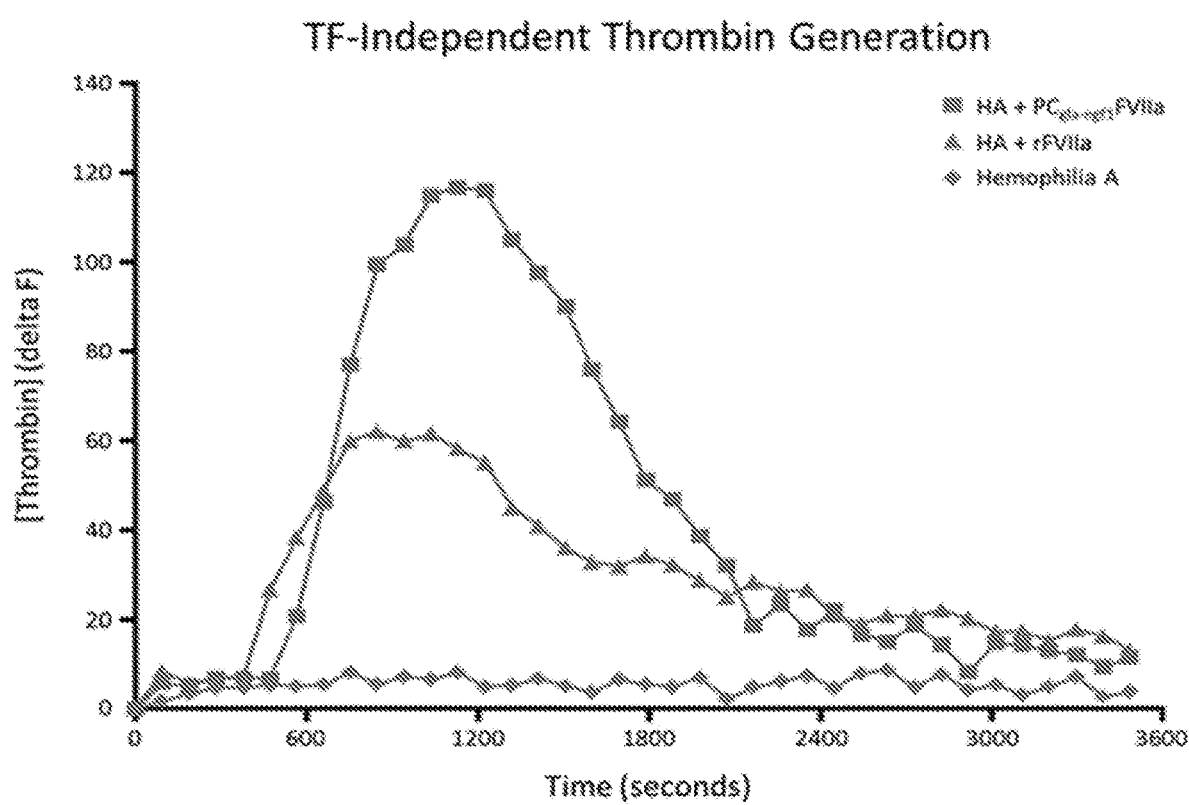
FIG. 9 shows that $PC_{gla-egf1}$FVIIa facilitates increased TF-independent thrombin generation compared to rFVIIa. Thrombin generation was assessed using a modified CAT assay in the absence of TF. Hemophilia A (HA) plasma was incubated with 20 μg/mL of $PC_{gla-egf1}$FVIIa (■), rFVIIa (▲), or buffer control (♦), followed by the addition of varying amounts of phospholipid vesicles (3-30 μM) in the presence of a fluorogenic thrombin substrate (432 μM). Thrombin generation was assessed by continuously monitoring the resulting change in fluorescence intensity as a result of substrate cleavage. Data shown are actual thrombin generation rates as a function of the change in fluorescence intensity over time.

Example 4. $PC_{gla-egf1}$FVIIa has Increased Tissue Factor (TF)-Independent Activity After confirming the ability of $PC_{gla-egf1}$FVIIa to cleave a synthetic peptide substrate, we also wanted to determine its ability to cleave a more physiologic substrate. We therefore compared the activity of $PC_{gla-egf1}$FVIIa to rFVIIa and to $FIX_{gla-egf1}$FVIIa on phospholipid vesicles (15% PS/41% PC/44% PE) by monitoring Factor X (FX) activation using a chromogenic substrate for Factor Xa (FXa) as described (Fager et al., 2018; Hoffman et al., 2011). $PC_{gla-egf1}$FVIIa, $FIX_{gla-egf1}$FVIIa, or rFVIIa (20 nM) were incubated with FX (135 nM), Pefachrome FXa (500 μM), and 5 mM $CaCl_2$ in the presence of 40 μM phospholipid. FXa activity was assessed by monitoring cleavage of the chromogenic substrate at 405 nm.

As shown in FIG. 6, the rate of FX activation by $PC_{gla-egf1}$FVIIa was significantly higher than that of both rFVIIa (~2.6 times) and $FIX_{gla-egf1}$FVIIa (~2 times). These results suggest the potential for increased hemostatic efficacy of $PC_{gla-egf1}$FVIIa compared to rFVIIa and $FIX_{gla-egf1}$FVIIa. This data demonstrates that EPCR is not required for PC-FVIIa binding to lipid membranes.

Example 5. $PC_{gla-egf1}$FVIIa has a Very Low Affinity for Tissue Factor (TF)

To determine the affinity of $PC_{gla-egf1}$FVIIa for TF, its TF-dependent activity was measured by monitoring FX activation in an assay designed to detect weak TF binding. For these assays, 2000 pM $PC_{gla-egf1}$FVIIa, 2000 pM $FIX_{gla-egf1}$FVIIa, or varying amounts of rFVIIa (0-2000 pM), were incubated with FX (135 nM), Pefachrome FXa (500 μM), and 5 mM $CaCl_2$ in the presence of 1 nM human TF (Innovin, DADE/Behring) which was dialyzed to remove excess calcium. FX activation was assessed by monitoring cleavage of the chromogenic substrate at 405 nm.

As shown in FIG. 7, the activity of $PC_{gla-egf1}$FVIIa was identical to the vehicle control indicating that the interaction between $PC_{gla-egf1}$FVIIa and TF is too weak to be measured. The very low level of FX activation by $PC_{gla-egf1}$FVIIa, even at 10- to 100-fold higher concentrations than that of rFVIIa, confirms that $PC_{gla-egf1}$FVIIa has a substantially reduced affinity for TF.

This reduced affinity for TF represents a potential advantage for $PC_{gla-egf1}$FVIIa, as long-term exposure to high levels of FVIIa causes premature mortality due to thrombosis in TF-rich tissues (Aljamali et al., 2008) and with TF-bearing microparticles. Minimizing the interaction with TF could lead to a decreased risk of thrombosis that can occur with rFVIIa (von Bruhl et al., 2012), particularly in non-hemophilia patients who are at higher risk for these complications (Yank et al., 2011).

Example 6. Hemostatic Activity of $PC_{gla-egf1}$FVIIa is Sensitive to Lipid Concentration Thrombin serves as the central regulator of hemostasis and thrombosis. The efficient generation of thrombin requires the assembly of multiprotein enzyme complexes that are assembled on an appropriate membrane surface. We therefore used a calibrated automated thrombography (CAT) assay as described (Vavalle et al., 2014), to determine the effect of varied concentrations of phospholipid surfaces on the ability of $PC_{gla-egf1}$FVIIa to facilitate thrombin generation. Briefly, Factor VIII deficient (hemophilia A) plasma was incubated with tissue factor (1 pM) and either rFVIIa (20 μg/ml), $PC_{gla-egf1}$FVIIa (20 μg/ml), or FVIII (2 U/ml) in the presence of varied concentrations of phospholipid vesicles (4-300 μM) and 432 μM fluorogenic thrombin substrate (Z-Gly-Gly-Arg-AMC). The lag time, peak thrombin concentration, and endogenous thrombin potential were then determined from direct measurement of the resulting change in fluorescence intensity over time.

As shown in FIG. 8A, thrombin generation in normal plasma is relatively insensitive to the available lipid concentration. However, the abilities of both rFVIIa (FIG. 8C) and $PC_{gla-egf1}$FVIIa (FIG. 8D) to facilitate thrombin generation in Hemophilia A (FVIII deficient) plasma are quite sensitive to the lipid concentration with maximum activity noted in the 300 μM phospholipid range. Furthermore, while rFVIIa considerably shortens the lag time (FIG. 8A vs. FIG. 8C), the $PC_{gla-egf1}$FVIIa does not, likely due to the binding of rFVIIa but not $PC_{gla-egf1}$FVIIa to TF.

Example 7. $PC_{gla-egf1}$FVIIa Facilitates Increased TF-Independent Thrombin Generation Given the increased rate of TF-independent FX activation by $PC_{gla-egf1}$FVIIa as compared to rFVIIa, we wanted to confirm that this would translate into an increased ability to facilitate thrombin generation. To do so, we used a modification of the CAT assay described in Example 6 in which the TF was excluded. Briefly, Hemophilia A plasma was incubated with either rFVIIa (20 μg/ml) or $PC_{gla-egf1}$FVIIa (20 μg/ml), in the presence of phospholipid vesicles (3-30 μM) and a fluorogenic thrombin substrate (432 μM). The lag time, peak thrombin concentration, and endogenous thrombin potential were again determined from direct measurement of the resulting change in fluorescence intensity over time.

As shown in FIG. 9, in the absence of TF, no appreciable thrombin generation was seen in hemophilia A plasma alone. However, the addition of either rFVIIa or PC$_{gla-egf1}$FVIIa resulted in significantly increased thrombin generation. Furthermore, the addition of PC$_{gla-egf1}$FVIIa resulted in increased peak thrombin concentration and endogenous thrombin potential with a longer lag time compared to rFVIIa in this experiment. The increase in TF-independent thrombin generation observed in the in vitro thrombin generation (CAT) assay suggests the potential for increased hemostatic efficacy of PC$_{gla-egf1}$FVIIa compared to rFVIIa. In addition, the lack of measurable TF-dependent activity also suggests that PC$_{gla-egf1}$FVIIa has the potential for decreased thrombogenicity compared to rFVIIa.

REFERENCES

Aljamali M N, et al. Long-term expression of murine activated factor VII is safe, but elevated levels cause premature mortality. *J. Clin. Invest.* 118:1825-1834 (2008).

Chang J Y, et al. The roles of factor VII's structural domains in tissue factor binding. *Biochemistry* 34:12227-12232 (1995).

Fager A M, et al. Human platelets express endothelial protein C receptor, which can be utilized to enhance localization of factor VIIa activity. *J. Thromb. Haemost.* 16:1817-1829 (2018).

Fukudome K, et al. Identification, cloning, and regulation of a novel endothelial cell protein C/activated protein C receptor. *J. Biol. Chem.* 269:26486-26491 (1994).

Ghosh S, et al. Endothelial cell protein C receptor acts as a cellular receptor for factor VIIa on endothelium. *J. Biol. Chem.* 282:11849-11857 (2007).

Grandoni J, et al. Kinetic analysis and binding studies of a new recombinant human factor VIIa for treatment of haemophilia. *Haemophilia* 23:300-308 (2017).

Hedner U. Recombinant activated factor VII as a universal haemostatic agent. *Blood Coagul. Fibrinolysis. March;* 9 Suppl 1:S147-152 (1998).

Hoffman M, et al. Platelet binding and activity of a factor VIIa variant with enhanced tissue factor independent activity. *J. Thromb. Haemost.* 9:759-766 (2011).

Jin J, et al. Factor VIIa's first epidermal growth factor-like domain's role in catalytic activity. *Biochemistry* 38:1185-1192 (1999).

Kaufman R J. Post-translational Modifications Required for Coagulation Factor Secretion and Function. *Thromb. Haemost.* 79:1068-1079 (1998).

Keshava S, et al. Factor VIIa interaction with EPCR modulates the hemostatic effect of rFVIIa in hemophilia therapy: mode of its action. *Blood Adv.* 1:1206-1214 (2017).

Kisiel W. Human Plasma Protein C. *J. Clin. Invest.* 64:761-769 (1979).

Kriegler T, et al. Measuring Endoplasmic Reticulum Signal Sequences Translocation Efficiency Using the Xbp1 Arrest Peptide. *Cell Chem. Biol.* 25:880-890 (2018).

Lazarus R A, et al. Inhibitors of Tissue Factor-Factor VIIa for Anticoagulant Therapy. *Curr. Med. Chem.* 11:2275-2290 (2004).

Monroe D M, et al. Platelet activity of high-dose Factor VIIa is independent of tissue factor. *Br. J. Haematol.* 99:542-547 (1997).

Pan L C, et al. The propeptide of rat bone gamma-carboxyglutamic acid protein shares homology with other vitamin K-dependent protein precursors. *Proc. Natl. Acad. Sci. USA* 82:6109-6113 (1985).

Stanley T B, et al. The Propeptides of the Vitamin K-dependent Proteins Possess Different Affinities for the Vitamin K-dependent Carboxylase. *J. Biol. Chem.* 274:16940-16944 (1999).

Vavalle J P, et al. The effect of the REG2 Anticoagulation System on thrombin generation kinetics: a pharmacodynamic and pharmacokinetic first-in-human study. *J. Thromb. Thrombolysis* 38:275-284 (2014).

von Bruhl M L, et al. Monocytes, neutrophils, and platelets cooperate to initiate and propagate venous thrombosis in mice in vivo. *J. Exp. Med.* 209:819-835 (2012).

Yank V, et al. Systematic review: benefits and harms of in-hospital use of recombinant factor VIIa for off-label indications. *Ann. Intern Med.* 154:529-540 (2011).

The present invention is further described by the following claims.

What is claimed is:

1. A chimeric Protein C-Factor VII (PC-FVII) protein comprising a Gla domain of Protein C (PC), an EGF-1 domain of PC, an EGF-2 domain of Factor VII (FVII), and a protease domain of FVII,
wherein the chimeric PC-FVII protein comprises the amino acid sequence of SEQ ID NO: 6 and activates Factor X.

2. The chimeric PC-FVII protein of claim 1, wherein the light chain and the heavy chain are linked by a disulfide bond.

3. The chimeric PC-FVII protein of claim 1, wherein the Gla domain comprises the amino acid sequence set forth in SEQ ID NO: 9.

4. The chimeric PC-FVII protein of claim 1, wherein the EGF-1 domain comprises the amino acid sequence set forth in SEQ ID NO: 12.

5. The chimeric PC-FVII protein of claim 1, wherein the EGF-2 domain comprises the amino acid sequence set forth in SEQ ID NO: 11.

6. The chimeric PC-FVII protein of claim 1, wherein the protease domain comprises the amino acid sequence set forth in SEQ ID NO: 14.

7. The chimeric PC-FVII protein of claim 1, wherein the protease domain comprises the amino acid sequence set forth in SEQ ID NO: 15.

8. The chimeric PC-FVII protein of claim 1, further comprising a propeptide sequence, wherein the propeptide sequence binds vitamin K-dependent γ-glutamyl carboxylase.

9. The chimeric PC-FVII protein of claim 8, further comprising an endoplasmic reticulum translocalization signal peptide.

10. The chimeric PC-FVII protein of claim 9, wherein the PC-FVII protein comprises the amino acid sequence set forth in SEQ ID NO: 5.

11. A composition comprising the chimeric PC-FVII protein of claim 1.

12. The composition of claim 11, wherein the composition is a pharmaceutical composition.

* * * * *

SEQUENCE LISTING

<160> NUMBER OF SEQ ID NOS: 16

<210> SEQ ID NO 1
<211> LENGTH: 466
<212> TYPE: PRT
<213> ORGANISM: Homo sapiens

<400> SEQUENCE: 1

```
Met Val Ser Gln Ala Leu Arg Leu Leu Cys Leu Leu Leu Gly Leu Gln
1               5                   10                  15

Gly Cys Leu Ala Ala Gly Gly Val Ala Lys Ala Ser Gly Gly Glu Thr
            20                  25                  30

Arg Asp Met Pro Trp Lys Pro Gly Pro His Arg Val Phe Val Thr Gln
        35                  40                  45

Glu Glu Ala His Gly Val Leu His Arg Arg Arg Arg Ala Asn Ala Phe
    50                  55                  60

Leu Glu Glu Leu Arg Pro Gly Ser Leu Glu Arg Glu Cys Lys Glu Glu
65                  70                  75                  80

Gln Cys Ser Phe Glu Glu Ala Arg Glu Ile Phe Lys Asp Ala Glu Arg
```

```
            85                  90                  95
Thr Lys Leu Phe Trp Ile Ser Tyr Ser Asp Gly Asp Gln Cys Ala Ser
            100                 105                 110

Ser Pro Cys Gln Asn Gly Gly Ser Cys Lys Asp Gln Leu Gln Ser Tyr
            115                 120                 125

Ile Cys Phe Cys Leu Pro Ala Phe Glu Gly Arg Asn Cys Glu Thr His
            130                 135                 140

Lys Asp Asp Gln Leu Ile Cys Val Asn Glu Asn Gly Gly Cys Glu Gln
145                 150                 155                 160

Tyr Cys Ser Asp His Thr Gly Thr Lys Arg Ser Cys Arg Cys His Glu
            165                 170                 175

Gly Tyr Ser Leu Leu Ala Asp Gly Val Ser Cys Thr Pro Thr Val Glu
            180                 185                 190

Tyr Pro Cys Gly Lys Ile Pro Ile Leu Glu Lys Arg Asn Ala Ser Lys
            195                 200                 205

Pro Gln Gly Arg Ile Val Gly Gly Lys Val Cys Pro Lys Gly Glu Cys
            210                 215                 220

Pro Trp Gln Val Leu Leu Leu Val Asn Gly Ala Gln Leu Cys Gly Gly
225                 230                 235                 240

Thr Leu Ile Asn Thr Ile Trp Val Val Ser Ala Ala His Cys Phe Asp
            245                 250                 255

Lys Ile Lys Asn Trp Arg Asn Leu Ile Ala Val Leu Gly Glu His Asp
            260                 265                 270

Leu Ser Glu His Asp Gly Asp Glu Gln Ser Arg Arg Val Ala Gln Val
            275                 280                 285

Ile Ile Pro Ser Thr Tyr Val Pro Gly Thr Thr Asn His Asp Ile Ala
            290                 295                 300

Leu Leu Arg Leu His Gln Pro Val Val Leu Thr Asp His Val Val Pro
305                 310                 315                 320

Leu Cys Leu Pro Glu Arg Thr Phe Ser Glu Arg Thr Leu Ala Phe Val
            325                 330                 335

Arg Phe Ser Leu Val Ser Gly Trp Gly Gln Leu Leu Asp Arg Gly Ala
            340                 345                 350

Thr Ala Leu Glu Leu Met Val Leu Asn Val Pro Arg Leu Met Thr Gln
            355                 360                 365

Asp Cys Leu Gln Gln Ser Arg Lys Val Gly Asp Ser Pro Asn Ile Thr
            370                 375                 380

Glu Tyr Met Phe Cys Ala Gly Tyr Ser Asp Gly Ser Lys Asp Ser Cys
385                 390                 395                 400

Lys Gly Asp Ser Gly Gly Pro His Ala Thr His Tyr Arg Gly Thr Trp
            405                 410                 415

Tyr Leu Thr Gly Ile Val Ser Trp Gly Gln Gly Cys Ala Thr Val Gly
            420                 425                 430

His Phe Gly Val Tyr Thr Arg Val Ser Gln Tyr Ile Glu Trp Leu Gln
            435                 440                 445

Lys Leu Met Arg Ser Glu Pro Arg Pro Gly Val Leu Leu Arg Ala Pro
450                 455                 460

Phe Pro
465

<210> SEQ ID NO 2
<211> LENGTH: 406
<212> TYPE: PRT
<213> ORGANISM: Homo sapiens
```

<400> SEQUENCE: 2

```
Ala Asn Ala Phe Leu Glu Glu Leu Arg Pro Gly Ser Leu Glu Arg Glu
1               5                   10                  15

Cys Lys Glu Glu Gln Cys Ser Phe Glu Glu Ala Arg Glu Ile Phe Lys
            20                  25                  30

Asp Ala Glu Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
    130                 135                 140

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
        195                 200                 205

Gly Glu His Asp Leu Ser Glu His Asp Gly Asp Glu Gln Ser Arg Arg
    210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
            260                 265                 270

Leu Ala Phe Val Arg Phe Ser Leu Val Ser Gly Trp Gly Gln Leu Leu
        275                 280                 285

Asp Arg Gly Ala Thr Ala Leu Glu Leu Met Val Leu Asn Val Pro Arg
    290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
            340                 345                 350

Arg Gly Thr Trp Tyr Leu Thr Gly Ile Val Ser Trp Gly Gln Gly Cys
        355                 360                 365

Ala Thr Val Gly His Phe Gly Val Tyr Thr Arg Val Ser Gln Tyr Ile
    370                 375                 380

Glu Trp Leu Gln Lys Leu Met Arg Ser Glu Pro Arg Pro Gly Val Leu
385                 390                 395                 400

Leu Arg Ala Pro Phe Pro
```

<210> SEQ ID NO 3
<211> LENGTH: 461
<212> TYPE: PRT
<213> ORGANISM: Homo sapiens

<400> SEQUENCE: 3

```
Met Trp Gln Leu Thr Ser Leu Leu Phe Val Ala Thr Trp Gly Ile
1               5                   10                  15

Ser Gly Thr Pro Ala Pro Leu Asp Ser Val Phe Ser Ser Glu Arg
                20                  25                  30

Ala His Gln Val Leu Arg Ile Arg Lys Arg Ala Asn Ser Phe Leu Glu
                35                  40                  45

Glu Leu Arg His Ser Ser Leu Glu Arg Glu Cys Ile Glu Glu Ile Cys
        50                  55                  60

Asp Phe Glu Glu Ala Lys Glu Ile Phe Gln Asn Val Asp Asp Thr Leu
65                  70                  75                  80

Ala Phe Trp Ser Lys His Val Asp Gly Asp Gln Cys Leu Val Leu Pro
                85                  90                  95

Leu Glu His Pro Cys Ala Ser Leu Cys Cys Gly His Gly Thr Cys Ile
                100                 105                 110

Asp Gly Ile Gly Ser Phe Ser Cys Asp Cys Arg Ser Gly Trp Glu Gly
                115                 120                 125

Arg Phe Cys Gln Arg Glu Val Ser Phe Leu Asn Cys Ser Leu Asp Asn
130                 135                 140

Gly Gly Cys Thr His Tyr Cys Leu Glu Glu Val Gly Trp Arg Arg Cys
145                 150                 155                 160

Ser Cys Ala Pro Gly Tyr Lys Leu Gly Asp Asp Leu Leu Gln Cys His
                165                 170                 175

Pro Ala Val Lys Phe Pro Cys Gly Arg Pro Trp Lys Arg Met Glu Lys
                180                 185                 190

Lys Arg Ser His Leu Lys Arg Asp Thr Glu Asp Gln Glu Asp Gln Val
                195                 200                 205

Asp Pro Arg Leu Ile Asp Gly Lys Met Thr Arg Arg Gly Asp Ser Pro
                210                 215                 220

Trp Gln Val Val Leu Leu Asp Ser Lys Lys Lys Leu Ala Cys Gly Ala
225                 230                 235                 240

Val Leu Ile His Pro Ser Trp Val Leu Thr Ala Ala His Cys Met Asp
                245                 250                 255

Glu Ser Lys Lys Leu Leu Val Arg Leu Gly Glu Tyr Asp Leu Arg Arg
                260                 265                 270

Trp Glu Lys Trp Glu Leu Asp Leu Asp Ile Lys Glu Val Phe Val His
                275                 280                 285

Pro Asn Tyr Ser Lys Ser Thr Thr Asp Asn Asp Ile Ala Leu Leu His
                290                 295                 300

Leu Ala Gln Pro Ala Thr Leu Ser Gln Thr Ile Val Pro Ile Cys Leu
305                 310                 315                 320

Pro Asp Ser Gly Leu Ala Glu Arg Glu Leu Asn Gln Ala Gly Gln Glu
                325                 330                 335

Thr Leu Val Thr Gly Trp Gly Tyr His Ser Ser Arg Glu Lys Glu Ala
                340                 345                 350

Lys Arg Asn Arg Thr Phe Val Leu Asn Phe Ile Lys Ile Pro Val Val
                355                 360                 365
```

```
Pro His Asn Glu Cys Ser Glu Val Met Ser Asn Met Val Ser Glu Asn
    370                 375                 380

Met Leu Cys Ala Gly Ile Leu Gly Asp Arg Gln Asp Ala Cys Glu Gly
385                 390                 395                 400

Asp Ser Gly Gly Pro Met Val Ala Ser Phe His Gly Thr Trp Phe Leu
                    405                 410                 415

Val Gly Leu Val Ser Trp Gly Glu Gly Cys Gly Leu Leu His Asn Tyr
                420                 425                 430

Gly Val Tyr Thr Lys Val Ser Arg Tyr Leu Asp Trp Ile His Gly His
                435                 440                 445

Ile Arg Asp Lys Glu Ala Pro Gln Lys Ser Trp Ala Pro
    450                 455                 460
```

<210> SEQ ID NO 4
<211> LENGTH: 419
<212> TYPE: PRT
<213> ORGANISM: Homo sapiens

<400> SEQUENCE: 4

```
Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
            20                  25                  30

Asn Val Asp Asp Thr Leu Ala Phe Trp Ser Lys His Val Asp Gly Asp
                35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
130                 135                 140

Trp Lys Arg Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Arg Arg Gly Asp Ser Pro Trp Gln Val Val Leu Leu Asp Ser Lys Lys
            180                 185                 190

Lys Leu Ala Cys Gly Ala Val Leu Ile His Pro Ser Trp Val Leu Thr
        195                 200                 205

Ala Ala His Cys Met Asp Glu Ser Lys Lys Leu Leu Val Arg Leu Gly
    210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285
```

```
Asn Gln Ala Gly Gln Glu Thr Leu Val Thr Gly Trp Gly Tyr His Ser
        290                 295                 300
Ser Arg Glu Lys Glu Ala Lys Arg Asn Arg Thr Phe Val Leu Asn Phe
305                 310                 315                 320
Ile Lys Ile Pro Val Val Pro His Asn Glu Cys Ser Gly Val Met Ser
                325                 330                 335
Asn Met Val Ser Glu Asn Met Leu Cys Ala Gly Ile Leu Gly Asp Arg
        340                 345                 350
Gln Asp Ala Cys Glu Gly Asp Ser Gly Gly Pro Met Val Ala Ser Phe
            355                 360                 365
His Gly Thr Trp Phe Leu Val Gly Leu Val Ser Trp Gly Glu Gly Cys
        370                 375                 380
Gly Leu Leu His Asn Tyr Gly Val Tyr Thr Lys Val Ser Arg Tyr Leu
385                 390                 395                 400
Asp Trp Ile His Gly His Ile Arg Asp Lys Glu Ala Pro Gln Lys Ser
                405                 410                 415
Trp Ala Pro

<210> SEQ ID NO 5
<211> LENGTH: 455
<212> TYPE: PRT
<213> ORGANISM: Artificial Sequence
<220> FEATURE:
<223> OTHER INFORMATION: PCgla-egf1FVII chimeric zymogen
<220> FEATURE:
<221> NAME/KEY: MISC_FEATURE
<222> LOCATION: (1)..(133)
<223> OTHER INFORMATION: amino acid residues from PC
<220> FEATURE:
<221> NAME/KEY: MISC_FEATURE
<222> LOCATION: (134)..(455)
<223> OTHER INFORMATION: amino acid residues from FVII
<220> FEATURE:
<221> NAME/KEY: MISC_FEATURE
<222> LOCATION: (201)..(202)
<223> OTHER INFORMATION: FVII activation site

<400> SEQUENCE: 5

Met Trp Gln Leu Thr Ser Leu Leu Leu Phe Val Ala Thr Trp Gly Ile
1               5                   10                  15
Ser Gly Thr Pro Ala Pro Leu Asp Ser Val Phe Ser Ser Ser Glu Arg
            20                  25                  30
Ala His Gln Val Leu Arg Ile Arg Lys Arg Ala Asn Ser Phe Leu Glu
        35                  40                  45
Glu Leu Arg His Ser Ser Leu Glu Arg Glu Cys Ile Glu Glu Ile Cys
    50                  55                  60
Asp Phe Glu Glu Ala Lys Glu Ile Phe Gln Asn Val Asp Asp Thr Leu
65                  70                  75                  80
Ala Phe Trp Ser Lys His Val Asp Gly Asp Gln Cys Leu Val Leu Pro
                85                  90                  95
Leu Glu His Pro Cys Ala Ser Leu Cys Cys Gly His Gly Thr Cys Ile
            100                 105                 110
Asp Gly Ile Gly Ser Phe Ser Cys Asp Cys Arg Ser Gly Trp Glu Gly
        115                 120                 125
Arg Phe Cys Gln Arg Lys Asp Asp Gln Leu Ile Cys Val Asn Glu Asn
    130                 135                 140
Gly Gly Cys Glu Gln Tyr Cys Ser Asp His Thr Gly Thr Lys Arg Ser
145                 150                 155                 160
```

```
Cys Arg Cys His Glu Gly Tyr Ser Leu Leu Ala Asp Gly Val Ser Cys
                165                 170                 175

Thr Pro Thr Val Glu Tyr Pro Cys Gly Lys Ile Pro Ile Leu Glu Lys
            180                 185                 190

Arg Asn Ala Ser Lys Pro Gln Gly Arg Ile Val Gly Gly Lys Val Cys
        195                 200                 205

Pro Lys Gly Glu Cys Pro Trp Gln Val Leu Leu Leu Val Asn Gly Ala
    210                 215                 220

Gln Leu Cys Gly Gly Thr Leu Ile Asn Thr Ile Trp Val Val Ser Ala
225                 230                 235                 240

Ala His Cys Phe Asp Lys Ile Lys Asn Trp Arg Asn Leu Ile Ala Val
                245                 250                 255

Leu Gly Glu His Asp Leu Ser Glu His Asp Gly Asp Glu Gln Ser Arg
            260                 265                 270

Arg Val Ala Gln Val Ile Ile Pro Ser Thr Tyr Val Pro Gly Thr Thr
        275                 280                 285

Asn His Asp Ile Ala Leu Leu Arg Leu His Gln Pro Val Val Leu Thr
    290                 295                 300

Asp His Val Val Pro Leu Cys Leu Pro Glu Arg Thr Phe Ser Glu Arg
305                 310                 315                 320

Thr Leu Ala Phe Val Arg Phe Ser Leu Val Ser Gly Trp Gly Gln Leu
                325                 330                 335

Leu Asp Arg Gly Ala Thr Ala Leu Glu Leu Met Val Leu Asn Val Pro
            340                 345                 350

Arg Leu Met Thr Gln Asp Cys Leu Gln Gln Ser Arg Lys Val Gly Asp
        355                 360                 365

Ser Pro Asn Ile Thr Glu Tyr Met Phe Cys Ala Gly Tyr Ser Asp Gly
    370                 375                 380

Ser Lys Asp Ser Cys Lys Gly Asp Ser Gly Gly Pro His Ala Thr His
385                 390                 395                 400

Tyr Arg Gly Thr Trp Tyr Leu Thr Gly Ile Val Ser Trp Gly Gln Gly
                405                 410                 415

Cys Ala Thr Val Gly His Phe Gly Val Tyr Thr Arg Val Ser Gln Tyr
            420                 425                 430

Ile Glu Trp Leu Gln Lys Leu Met Arg Ser Glu Pro Arg Pro Gly Val
        435                 440                 445

Leu Leu Arg Ala Pro Phe Pro
    450                 455

<210> SEQ ID NO 6
<211> LENGTH: 413
<212> TYPE: PRT
<213> ORGANISM: Artificial Sequence
<220> FEATURE:
<223> OTHER INFORMATION: PCgla-egf1FVIIa chimera
<220> FEATURE:
<221> NAME/KEY: MISC_FEATURE
<222> LOCATION: (1)..(91)
<223> OTHER INFORMATION: amino acid residues from PC
<220> FEATURE:
<221> NAME/KEY: MISC_FEATURE
<222> LOCATION: (92)..(413)
<223> OTHER INFORMATION: amino acid sequences from FVII
<220> FEATURE:
<221> NAME/KEY: MISC_FEATURE
<222> LOCATION: (159)..(160)
<223> OTHER INFORMATION: FVII activation site

<400> SEQUENCE: 6
```

-continued

```
Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
            20                  25                  30

Asn Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Lys Asp Asp Gln Leu
                85                  90                  95

Ile Cys Val Asn Glu Asn Gly Gly Cys Glu Gln Tyr Cys Ser Asp His
            100                 105                 110

Thr Gly Thr Lys Arg Ser Cys Arg Cys His Glu Gly Tyr Ser Leu Leu
        115                 120                 125

Ala Asp Gly Val Ser Cys Thr Pro Thr Val Glu Tyr Pro Cys Gly Lys
    130                 135                 140

Ile Pro Ile Leu Glu Lys Arg Asn Ala Ser Lys Pro Gln Gly Arg Ile
145                 150                 155                 160

Val Gly Gly Lys Val Cys Pro Lys Gly Glu Cys Pro Trp Gln Val Leu
                165                 170                 175

Leu Leu Val Asn Gly Ala Gln Leu Cys Gly Gly Thr Leu Ile Asn Thr
            180                 185                 190

Ile Trp Val Val Ser Ala Ala His Cys Phe Asp Lys Ile Lys Asn Trp
        195                 200                 205

Arg Asn Leu Ile Ala Val Leu Gly Glu His Asp Leu Ser Glu His Asp
    210                 215                 220

Gly Asp Glu Gln Ser Arg Arg Val Ala Gln Val Ile Ile Pro Ser Thr
225                 230                 235                 240

Tyr Val Pro Gly Thr Thr Asn His Asp Ile Ala Leu Leu Arg Leu His
                245                 250                 255

Gln Pro Val Val Leu Thr Asp His Val Val Pro Leu Cys Leu Pro Glu
            260                 265                 270

Arg Thr Phe Ser Glu Arg Thr Leu Ala Phe Val Arg Phe Ser Leu Val
        275                 280                 285

Ser Gly Trp Gly Gln Leu Leu Asp Arg Gly Ala Thr Ala Leu Glu Leu
    290                 295                 300

Met Val Leu Asn Val Pro Arg Leu Met Thr Gln Asp Cys Leu Gln Gln
305                 310                 315                 320

Ser Arg Lys Val Gly Asp Ser Pro Asn Ile Thr Glu Tyr Met Phe Cys
                325                 330                 335

Ala Gly Tyr Ser Asp Gly Ser Lys Asp Ser Cys Lys Gly Asp Ser Gly
            340                 345                 350

Gly Pro His Ala Thr His Tyr Arg Gly Thr Trp Tyr Leu Thr Gly Ile
        355                 360                 365

Val Ser Trp Gly Gln Gly Cys Ala Thr Val Gly His Phe Gly Val Tyr
    370                 375                 380

Thr Arg Val Ser Gln Tyr Ile Glu Trp Leu Gln Lys Leu Met Arg Ser
385                 390                 395                 400

Glu Pro Arg Pro Gly Val Leu Leu Arg Ala Pro Phe Pro
                405                 410
```

<210> SEQ ID NO 7
<211> LENGTH: 1386
<212> TYPE: DNA
<213> ORGANISM: Artificial Sequence
<220> FEATURE:
<223> OTHER INFORMATION: cDNA sequence encoding the PCgla-egf1FVII chimeric zymogen

<400> SEQUENCE: 7

```
gtggaattca tgtggcagct cacaagcctc ctgctgttcg tggccacctg gggaatttcc      60
ggcacaccag ctcctcttga ctcagtgttc tccagcagcg agcgtgccca ccaggtgctg     120
cggatccgca acgtgccaa ctccttcctg gaggagctcc gtcacagcag cctggagcgg     180
gagtgcatag aggagatctg tgacttcgag gaggccaagg aaattttcca aaatgtggat     240
gacacactgg ccttctggtc caagcacgtc gacggtgacc agtgcttggt cttgcccttg     300
gagcacccgt gcgccagcct gtgctgcggg cacggcacgt gcatcgacgg catcggcagc     360
ttcagctgcg actgccgcag cggctgggag ggccgcttct gccagcgcaa ggatgaccag     420
ctgatctgtg tgaacgagaa cggcggctgt gagcagtact gcagtgacca cacgggcacc     480
aagcgctcct gtcggtgcca cgaggggtac tctctgctgg cagacggggt gtcctgcaca     540
cccacagttg aatatccatg tggaaaaata cctattctag aaaaaagaaa tgccagcaaa     600
ccccaaggcc gaattgtggg gggcaaggtg tgccccaaag gggagtgtcc atggcaggtc     660
ctgttgttgg tgaatggagc tcagttgtgt gggggggaccc tgatcaacac catctgggtg     720
gtctccgcgg cccactgttt cgacaaaatc aagaactgga ggaacctgat cgcggtgctg     780
ggcgagcacg acctcagcga gcacgacggg atgagcagag accggcgggt ggcgcaggtc     840
atcatcccca gcacgtacgt cccgggcacc accaaccacg acatcgcgct gctccgcctg     900
caccagcccg tggtcctcac tgaccatgtg gtgcccctct gcctgccgga acggacgttc     960
tctgagagga cgctggcctt cgtgcgcttc tcattggtca gcggctgggg ccagctgctg    1020
gaccgtggcg ccacggccct ggagctcatg gtcctcaacg tgccccggct gatgacccag    1080
gactgcctgc agcagtcacg gaaggtggga gactccccaa atatcacgga gtacatgttc    1140
tgtgccggct actcggatgg cagcaaggac tcctgcaagg gggacagtgg aggcccacat    1200
gccacccact accggggcac gtggtacctg acgggcatcg tcagctgggg ccagggctgc    1260
gcaaccgtgg gccactttgg ggtgtacacc agggtctccc agtacatcga gtggctgcaa    1320
aagctcatgc gctcagagcc acgcccagga gtcctcctgc gagccccatt tcccctagctc    1380
gagtct                                                                1386
```

<210> SEQ ID NO 8
<211> LENGTH: 45
<212> TYPE: PRT
<213> ORGANISM: Artificial Sequence
<220> FEATURE:
<223> OTHER INFORMATION: FVII Gla domain

<400> SEQUENCE: 8

```
Ala Asn Ala Phe Leu Glu Glu Leu Arg Pro Gly Ser Leu Glu Arg Glu
1               5                   10                  15

Cys Lys Glu Glu Gln Cys Ser Phe Glu Glu Ala Arg Glu Ile Phe Lys
            20                  25                  30

Asp Ala Glu Arg Thr Lys Leu Phe Trp Ile Ser Tyr Ser
        35                  40                  45
```

<210> SEQ ID NO 9

```
<211> LENGTH: 46
<212> TYPE: PRT
<213> ORGANISM: Artificial Sequence
<220> FEATURE:
<223> OTHER INFORMATION: PC Gla domain

<400> SEQUENCE: 9

Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
            20                  25                  30

Asn Val Asp Asp Thr Leu Ala Phe Trp Ser Lys His Val Asp
        35                  40                  45

<210> SEQ ID NO 10
<211> LENGTH: 37
<212> TYPE: PRT
<213> ORGANISM: Artificial Sequence
<220> FEATURE:
<223> OTHER INFORMATION: FVII EGF-1 domain

<400> SEQUENCE: 10

Asp Gly Asp Gln Cys Ala Ser Ser Pro Cys Gln Asn Gly Gly Ser Cys
1               5                   10                  15

Lys Asp Gln Leu Gln Ser Tyr Ile Cys Phe Cys Leu Pro Ala Phe Glu
            20                  25                  30

Gly Arg Asn Cys Glu
        35

<210> SEQ ID NO 11
<211> LENGTH: 42
<212> TYPE: PRT
<213> ORGANISM: Artificial Sequence
<220> FEATURE:
<223> OTHER INFORMATION: FVII EGF-2 domain

<400> SEQUENCE: 11

Asp Gln Leu Ile Cys Val Asn Glu Asn Gly Gly Cys Glu Gln Tyr Cys
1               5                   10                  15

Ser Asp His Thr Gly Thr Lys Arg Ser Cys Arg Cys His Glu Gly Tyr
            20                  25                  30

Ser Leu Leu Ala Asp Gly Val Ser Cys Thr
        35                  40

<210> SEQ ID NO 12
<211> LENGTH: 36
<212> TYPE: PRT
<213> ORGANISM: Artificial Sequence
<220> FEATURE:
<223> OTHER INFORMATION: PC EGF-1 domain

<400> SEQUENCE: 12

Leu Glu His Pro Cys Ala Ser Leu Cys Cys Gly His Gly Thr Cys Ile
1               5                   10                  15

Asp Gly Ile Gly Ser Phe Ser Cys Asp Cys Arg Ser Gly Trp Glu Gly
            20                  25                  30

Arg Phe Cys Gln
        35

<210> SEQ ID NO 13
<211> LENGTH: 41
<212> TYPE: PRT
<213> ORGANISM: Artificial Sequence
```

<220> FEATURE:
<223> OTHER INFORMATION: PC-EGF-2 domain

<400> SEQUENCE: 13

Ser Phe Leu Asn Cys Ser Leu Asp Asn Gly Gly Cys Thr His Tyr Cys
1               5                   10                  15

Leu Glu Glu Val Gly Trp Arg Arg Cys Ser Cys Ala Pro Gly Tyr Lys
            20                  25                  30

Leu Gly Asp Asp Leu Leu Gln Cys His
        35                  40

<210> SEQ ID NO 14
<211> LENGTH: 240
<212> TYPE: PRT
<213> ORGANISM: Artificial Sequence
<220> FEATURE:
<223> OTHER INFORMATION: FVII Protease domain

<400> SEQUENCE: 14

Ile Val Gly Gly Lys Val Cys Pro Lys Gly Glu Cys Pro Trp Gln Val
1               5                   10                  15

Leu Leu Leu Val Asn Gly Ala Gln Leu Cys Gly Gly Thr Leu Ile Asn
            20                  25                  30

Thr Ile Trp Val Val Ser Ala Ala His Cys Phe Asp Lys Ile Lys Asn
        35                  40                  45

Trp Arg Asn Leu Ile Ala Val Leu Gly Glu His Asp Leu Ser Glu His
    50                  55                  60

Asp Gly Asp Glu Gln Ser Arg Arg Val Ala Gln Val Ile Ile Pro Ser
65                  70                  75                  80

Thr Tyr Val Pro Gly Thr Thr Asn His Asp Ile Ala Leu Leu Arg Leu
                85                  90                  95

His Gln Pro Val Val Leu Thr Asp His Val Val Pro Leu Cys Leu Pro
            100                 105                 110

Glu Arg Thr Phe Ser Glu Arg Thr Leu Ala Phe Val Arg Phe Ser Leu
        115                 120                 125

Val Ser Gly Trp Gly Gln Leu Leu Asp Arg Gly Ala Thr Ala Leu Glu
    130                 135                 140

Leu Met Val Leu Asn Val Pro Arg Leu Met Thr Gln Asp Cys Leu Gln
145                 150                 155                 160

Gln Ser Arg Lys Val Gly Asp Ser Pro Asn Ile Thr Glu Tyr Met Phe
                165                 170                 175

Cys Ala Gly Tyr Ser Asp Gly Ser Lys Asp Ser Cys Lys Gly Asp Ser
            180                 185                 190

Gly Gly Pro His Ala Thr His Tyr Arg Gly Thr Trp Tyr Leu Thr Gly
        195                 200                 205

Ile Val Ser Trp Gly Gln Gly Cys Ala Thr Val Gly His Phe Gly Val
    210                 215                 220

Tyr Thr Arg Val Ser Gln Tyr Ile Glu Trp Leu Gln Lys Leu Met Arg
225                 230                 235                 240

<210> SEQ ID NO 15
<211> LENGTH: 254
<212> TYPE: PRT
<213> ORGANISM: Artificial Sequence
<220> FEATURE:
<223> OTHER INFORMATION: FVII Protease domain

<400> SEQUENCE: 15

```
Ile Val Gly Gly Lys Val Cys Pro Lys Gly Glu Cys Pro Trp Gln Val
1               5                   10                  15

Leu Leu Leu Val Asn Gly Ala Gln Leu Cys Gly Gly Thr Leu Ile Asn
            20                  25                  30

Thr Ile Trp Val Val Ser Ala Ala His Cys Phe Asp Lys Ile Lys Asn
        35                  40                  45

Trp Arg Asn Leu Ile Ala Val Leu Gly Glu His Asp Leu Ser Glu His
    50                  55                  60

Asp Gly Asp Glu Gln Ser Arg Arg Val Ala Gln Val Ile Ile Pro Ser
65                  70                  75                  80

Thr Tyr Val Pro Gly Thr Thr Asn His Asp Ile Ala Leu Leu Arg Leu
                85                  90                  95

His Gln Pro Val Val Leu Thr Asp His Val Val Pro Leu Cys Leu Pro
                100                 105                 110

Glu Arg Thr Phe Ser Glu Arg Thr Leu Ala Phe Val Arg Phe Ser Leu
                115                 120                 125

Val Ser Gly Trp Gly Gln Leu Leu Asp Arg Gly Ala Thr Ala Leu Glu
            130                 135                 140

Leu Met Val Leu Asn Val Pro Arg Leu Met Thr Gln Asp Cys Leu Gln
145                 150                 155                 160

Gln Ser Arg Lys Val Gly Asp Ser Pro Asn Ile Thr Glu Tyr Met Phe
                165                 170                 175

Cys Ala Gly Tyr Ser Asp Gly Ser Lys Asp Ser Cys Lys Gly Asp Ser
                180                 185                 190

Gly Gly Pro His Ala Thr His Tyr Arg Gly Thr Trp Tyr Leu Thr Gly
            195                 200                 205

Ile Val Ser Trp Gly Gln Gly Cys Ala Thr Val Gly His Phe Gly Val
            210                 215                 220

Tyr Thr Arg Val Ser Gln Tyr Ile Glu Trp Leu Gln Lys Leu Met Arg
225                 230                 235                 240

Ser Glu Pro Arg Pro Gly Val Leu Leu Arg Ala Pro Phe Pro
                245                 250
```

<210> SEQ ID NO 16
<211> LENGTH: 239
<212> TYPE: PRT
<213> ORGANISM: Artificial Sequence
<220> FEATURE:
<223> OTHER INFORMATION: PC Protease domain

<400> SEQUENCE: 16

```
Leu Ile Asp Gly Lys Met Thr Arg Arg Gly Asp Ser Pro Trp Gln Val
1               5                   10                  15

Val Leu Leu Asp Ser Lys Lys Lys Leu Ala Cys Gly Ala Val Leu Ile
            20                  25                  30

His Pro Ser Trp Val Leu Thr Ala Ala His Cys Met Asp Glu Ser Lys
        35                  40                  45

Lys Leu Leu Val Arg Leu Gly Glu Tyr Asp Leu Arg Arg Trp Glu Lys
    50                  55                  60

Trp Glu Leu Asp Leu Asp Ile Lys Glu Val Phe Val His Pro Asn Tyr
65                  70                  75                  80

Ser Lys Ser Thr Thr Asp Asn Asp Ile Ala Leu Leu His Leu Ala Gln
                85                  90                  95

Pro Ala Thr Leu Ser Gln Thr Ile Val Pro Ile Cys Leu Pro Asp Ser
                100                 105                 110
```

-continued

```
Gly Leu Ala Glu Arg Glu Leu Asn Gln Ala Gly Gln Glu Thr Leu Val
        115                 120                 125
Thr Gly Trp Gly Tyr His Ser Ser Arg Glu Lys Glu Ala Lys Arg Asn
    130                 135                 140
Arg Thr Phe Val Leu Asn Phe Ile Lys Ile Pro Val Val Pro His Asn
145                 150                 155                 160
Glu Cys Ser Glu Val Met Ser Asn Met Val Ser Glu Asn Met Leu Cys
            165                 170                 175
Ala Gly Ile Leu Gly Asp Arg Gln Asp Ala Cys Glu Gly Asp Ser Gly
            180                 185                 190
Gly Pro Met Val Ala Ser Phe His Gly Thr Trp Phe Leu Val Gly Leu
        195                 200                 205
Val Ser Trp Gly Glu Gly Cys Gly Leu Leu His Asn Tyr Gly Val Tyr
    210                 215                 220
Thr Lys Val Ser Arg Tyr Leu Asp Trp Ile His Gly His Ile Arg
225                 230                 235
```